(12) United States Patent
Raven et al.

(10) Patent No.: US 8,888,732 B2
(45) Date of Patent: Nov. 18, 2014

(54) INTRALUMINAL SLEEVE WITH ACTIVE AGENTS

(75) Inventors: Joseph S. Raven, Goleta, CA (US); Janel A. Birk, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 429 days.

(21) Appl. No.: 13/046,615

(22) Filed: Mar. 11, 2011

(65) Prior Publication Data
US 2012/0232460 A1 Sep. 13, 2012

(51) Int. Cl.
*A61F 5/00* (2006.01)
*A61B 5/07* (2006.01)
*A61M 5/142* (2006.01)
*A61B 5/00* (2006.01)
*A61M 5/172* (2006.01)
*A61B 5/03* (2006.01)
*A61M 5/168* (2006.01)
*A61F 2/04* (2013.01)
*A61N 1/36* (2006.01)
*A61N 1/05* (2006.01)

(52) U.S. Cl.
CPC .......... *A61F 5/0076* (2013.01); *A61M 2205/50* (2013.01); *A61B 5/073* (2013.01); *A61M 2205/0294* (2013.01); *A61M 2230/005* (2013.01); *A61M 5/14276* (2013.01); *A61M 5/1684* (2013.01); *A61M 2210/1057* (2013.01); *A61F 2250/0001* (2013.01); *A61M 2205/3569* (2013.01); *A61M 2205/0244* (2013.01); *A61M 2205/8206* (2013.01); *A61F 2002/045* (2013.01); *A61M 2205/3523* (2013.01); *A61B 5/4839* (2013.01); *A61N 1/36057* (2013.01); *A61F 2250/0068* (2013.01); *A61N 1/0517* (2013.01); *A61B 5/4255* (2013.01); *A61M 2230/20* (2013.01); *A61B 5/746* (2013.01); *A61M 5/1723* (2013.01); *A61M 5/14224* (2013.01); *A61F 2/04* (2013.01); *A61M 2205/8243* (2013.01); *A61N 1/0509* (2013.01); *A61N 1/36085* (2013.01); *A61B 5/0031* (2013.01); *A61B 5/036* (2013.01); *A61M 2005/1726* (2013.01)
USPC ........................... 604/9; 690/890.1; 424/78.1

(58) Field of Classification Search
CPC ................. A61M 2205/054; A61M 2205/055; A61F 5/005; A61F 5/0036; A61F 5/0056; A61F 5/0076
USPC .............. 604/890.1, 890.11, 892, 9; 623/1.42
See application file for complete search history.

(56) References Cited

U.S. PATENT DOCUMENTS 1,702,974 A 2/1929 MacDonald
2,163,048 A 6/1939 McKee
(Continued)

FOREIGN PATENT DOCUMENTS

CN 1250382 4/2000
CN 1367670 9/2002
(Continued)

OTHER PUBLICATIONS

Perez, H.D., Mitrovic, B., et al. "Opportunities and Challenges of the Therapies Targeting CNS Regeneration". Volume 53 of Ernst Schering Foundation Symposium Proceedings. Springer: 2007. p. 3.*

(Continued)

*Primary Examiner* — Tatyana Zalukaeva
*Assistant Examiner* — Sara Sass
(74) *Attorney, Agent, or Firm* — Gordon & Jacobson, PC

(57) ABSTRACT

An intraluminal sleeve system is provided, which generally includes an intraluminal sleeve capable of dispensing an active agent to a patient, for example, a metabolic agent or satiety inducing agent. The intraluminal sleeve may be structured to contain the active agent and permit controlled release of the active agent to the patient while the intraluminal sleeve is positioned within the patient's intestine. Methods for treating obesity are also provided which include positioning an intraluminal sleeve in a patient's intestine, the intraluminal sleeve being capable of dispensing an active agent to the patient. In one embodiment, the active agent may be contained in a reservoir and dispensed to a portion of the patient's body.

21 Claims, 10 Drawing Sheets

(56) References Cited

U.S. PATENT DOCUMENTS

| | | | |
|---|---|---|---|
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders et al. |
| 4,118,805 A | 10/1978 | Reimels |
| 4,430,392 A | 2/1984 | Kelley et al. |
| 4,485,805 A | 12/1984 | Foster, Jr. |
| 4,545,367 A | 10/1985 | Tucci |
| 4,592,355 A | 6/1986 | Antebi |
| 4,598,699 A | 7/1986 | Garren et al. |
| 4,607,618 A | 8/1986 | Angelchik |
| 4,636,213 A | 1/1987 | Pakiam |
| 4,694,827 A | 9/1987 | Weiner et al. |
| 4,723,547 A | 2/1988 | Kullas et al. |
| 4,881,939 A | 11/1989 | Newman |
| 4,930,535 A | 6/1990 | Rinehold |
| 4,969,899 A | 11/1990 | Cox, Jr. |
| 5,074,868 A | 12/1991 | Kuzmak |
| 5,084,061 A | 1/1992 | Gau et al. |
| 5,211,371 A | 5/1993 | Coffee |
| 5,226,429 A | 7/1993 | Kuzmak |
| 5,289,817 A | 3/1994 | Williams et al. |
| 5,449,368 A | 9/1995 | Kuzmak |
| 5,527,340 A | 6/1996 | Vogel |
| 5,601,604 A | 2/1997 | Vincent |
| 5,658,298 A | 8/1997 | Vincent et al. |
| 5,693,014 A | 12/1997 | Abele et al. |
| 5,725,507 A | 3/1998 | Petrick |
| 5,748,200 A | 5/1998 | Funahashi |
| 5,819,749 A | 10/1998 | Lee et al. |
| RE36,176 E | 3/1999 | Kuzmak |
| 5,938,669 A | 8/1999 | Klaiber et al. |
| 6,074,341 A | 6/2000 | Anderson et al. |
| 6,102,678 A | 8/2000 | Peclat |
| 6,102,897 A | 8/2000 | Lang |
| 6,102,922 A | 8/2000 | Jakobsson et al. |
| 6,152,922 A | 11/2000 | Ouchi |
| 6,290,575 B1 | 9/2001 | Shipp |
| 6,454,699 B1 | 9/2002 | Forsell |
| 6,454,785 B2 | 9/2002 | De Hoyos Garza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,547,801 B1 | 4/2003 | Dargent et al. |
| 6,579,301 B1 | 6/2003 | Bales et al. |
| 6,629,776 B2 | 10/2003 | Bell et al. |
| 6,733,512 B2 | 5/2004 | McGhan |
| 6,733,513 B2 | 5/2004 | Boyle et al. |
| 6,746,460 B2 | 6/2004 | Gannoe et al. |
| 6,840,257 B2 | 1/2005 | Dario et al. |
| 6,994,095 B2 | 2/2006 | Burnett |
| 7,020,531 B1 | 3/2006 | Colliou et al. |
| 7,037,344 B2 | 5/2006 | Kagan et al. |
| 7,056,305 B2 | 6/2006 | Garza |
| 7,214,233 B2 | 5/2007 | Gannoe et al. |
| 7,785,635 B1 * | 8/2010 | Boileau et al. ............... 424/558 |
| 2002/0095181 A1 | 7/2002 | Beyar |
| 2002/0139208 A1 | 10/2002 | Yatskov |
| 2002/0183782 A1 | 12/2002 | Tsugita et al. |
| 2003/0073880 A1 | 4/2003 | Polsky et al. |
| 2003/0106761 A1 | 6/2003 | Taylor |
| 2005/0055039 A1 | 3/2005 | Burnett et al. |
| 2005/0131485 A1 | 6/2005 | Knudson et al. |
| 2005/0190070 A1 | 9/2005 | Rudduck et al. |
| 2005/0192615 A1 | 9/2005 | Torre et al. |
| 2005/0240279 A1 | 10/2005 | Kagan et al. |
| 2005/0250979 A1 | 11/2005 | Coe |
| 2005/0261711 A1 | 11/2005 | Okada et al. |
| 2005/0267595 A1 | 12/2005 | Chen et al. |
| 2005/0267596 A1 | 12/2005 | Chen et al. |
| 2006/0020278 A1 | 1/2006 | Burnett et al. |
| 2006/0025799 A1 | 2/2006 | Basu |
| 2006/0069403 A1 | 3/2006 | Shalon et al. |
| 2006/0142700 A1 | 6/2006 | Sobelman et al. |
| 2006/0184207 A1 * | 8/2006 | Darvish et al. ............... 607/40 |
| 2006/0229702 A1 | 10/2006 | Agnew |
| 2007/0016262 A1 | 1/2007 | Gross et al. |
| 2007/0083224 A1 | 4/2007 | Hively |
| 2007/0135829 A1 | 6/2007 | Paganon |
| 2007/0147170 A1 | 6/2007 | Hood et al. |
| 2007/0156248 A1 | 7/2007 | Marco et al. |
| 2007/0173881 A1 | 7/2007 | Birk et al. |
| 2007/0179556 A1 * | 8/2007 | Ben Haim et al. ............ 607/40 |
| 2007/0198074 A1 * | 8/2007 | Dann et al. ............... 623/1.11 |
| 2007/0288033 A1 | 12/2007 | Murature et al. |
| 2008/0172079 A1 | 7/2008 | Birk |
| 2008/0208240 A1 | 8/2008 | Paz |
| 2008/0243071 A1 | 10/2008 | Quijano et al. |
| 2008/0255601 A1 | 10/2008 | Birk |
| 2009/0131968 A1 | 5/2009 | Birk |
| 2009/0259246 A1 | 10/2009 | Eskaros et al. |
| 2010/0087843 A1 | 4/2010 | Bertolote et al. |
| 2010/0100079 A1 | 4/2010 | Berckan et al. |
| 2010/0168783 A1 | 7/2010 | Murature et al. |
| 2010/0174307 A1 | 7/2010 | Birk |
| 2010/0274194 A1 | 10/2010 | Sobelman et al. |

FOREIGN PATENT DOCUMENTS

| | | |
|---|---|---|
| DE | 8804765 | 5/1989 |
| DE | 102007025312 | 11/2008 |
| EP | 1396242 | 3/2004 |
| EP | 1396243 | 3/2004 |
| EP | 1774929 | 4/2007 |
| EP | 2095798 | 9/2009 |
| FR | 2797181 | 2/2001 |
| FR | 2823663 | 10/2002 |
| FR | 2852821 | 10/2004 |
| FR | 2855744 | 12/2004 |
| FR | 2941617 | 8/2010 |
| GB | 2086792 | 5/1982 |
| JP | 63-279854 | 11/1988 |
| JP | 1049572 | 2/1989 |
| JP | 63-264078 | 10/1998 |
| WO | WO 00/15158 | 3/2000 |
| WO | WO 01/10359 | 2/2001 |
| WO | WO 01/49245 | 7/2001 |
| WO | WO 01/66166 | 9/2001 |
| WO | WO 02/35980 | 5/2002 |
| WO | WO 03/055419 | 7/2003 |
| WO | WO 03/105732 | 12/2003 |
| WO | WO 2004/019671 | 3/2004 |
| WO | WO 2005/007231 | 1/2005 |
| WO | WO 2006/020370 | 6/2006 |
| WO | WO 2006/063593 | 6/2006 |
| WO | WO 2006/090018 | 8/2006 |
| WO | WO 2006/118744 | 11/2006 |
| WO | WO 2007/011086 | 10/2007 |
| WO | WO 2010/042062 | 4/2010 |

OTHER PUBLICATIONS

Xanthakos, "Bariatric surgery for extreme adolescent obesity: Indications, outcomes, and physiologic effects on the gut-brain axis", Elsevier Pathophysiology 15, 2008, pp. 135-146.

Baggio et al. "Biology of Integrins: GLP-1 and GIP"; Gastroenrology; V. 132; pp. 2131-2157; 2007.

Berne et al.; "Physiology"; V. 5; pp. 55-57, 210, 428 540, 579, 584, 591; 2004.

Boulant et al.; "Cholecystokinin in Transient Lower Oesophageal Sphincter Relation Due to Gastric Distension in Humans"; Gut; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Chaudri, Owais; "Can Gut Hormones Control Appetite and Prevent Obesity?" Diabetes Care, V. 31, Supp. 2, Feb. 2008.

Cohen et al.; "Oxyntomodulin Suppresses Appetite and Reduces Food in Humans"; J. Clin. Endocrinol. Metab.; V. 88; pp. 4696-4701; 2003.

Dakin et al.; "Oxyntomodulin Inhibits Food Intake in the Rat"; Endocrinology; V. 142; pp. 4244-4250; 2001.

(56) References Cited

OTHER PUBLICATIONS

Dakin et al.; "Peripheral Oxyntomodulin Reduces Food Intake and Body Weight gain in Rats" Endocrinology; V. 145; pp. 2687-2695; 2004.

Davison, J.; "Activation of Vagal-Gastric Mechanoreceptors by Cholecystokinin"; Proc. West. Pharmocol. Soc.; V. 29; pp. 363-366; 1986.

Ekblad et al.; "Distribution of Pancreatic Peptide and Peptide-YY"; Peptides; V. 23; pp. 251-261; 2002.

Greenough et al.; "Untangling the Effects of Hunger, Anxiety and Nausea on Energy Intake During Intravenous Cholecystokinin Octapeptide (CCK-8) Infusion" Physiology and Behavior; V. 65 (2); pp. 303-310, 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; "Gastrointestinal Factors in Hunger and Satiety"; Neurosci. and Behav. Rev.; V. 6; pp. 145-164; 1982.

Kissileff et al.; "Peptides that Regulate Food Intake: Cholecystokinin and Stomach Distension Combine to Reduce Food Intake in Humans"; Am. J. Physiol. Regul. Integr. Comp. Physiol.; V. 285; pp. 992-998; 2003.

Naslund et al.; "Prandial Subcutaneous Injection of Glucagon-Like Peptide"; Br. J. Nutr.; V. 91; pp. 439-446; 2004.

Renshaw et al. "Peptide YY: A Potential Therapy for Obesity"; Current Drug Targets; V. 6; pp. 171-179; 2005.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; 2001.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

BIB Bioenterics Intragastric Balloon Program, "Take Control of Your Weight and Your Life/The Solution for You," Inamed Health, pp. 1-2; Jan. 19, 2004.

BIB Bioenterics Intragastric Balloon Program, "Taking the Next Step/Take Control of Your Weight and Your Life," Inamed Health, pp. 1-9; Apr. 29, 2004.

BIB Data Sheet Directions for Use, "BioEnterics Intragastric Balloon System," Inamed Health, 1-12 pp.

"Living With the Bib/BioEnterics Intragastric Balloon Program," Inamed Health; 1-10 Patient Information Brochure; pp.; May 1, 2005.

\* cited by examiner

INTRALUMINAL SLEEVE WITH ACTIVE AGENTS

FIELD

The present invention relates to intraluminal sleeves for the treatment of obesity and obesity related disorders, and more specifically relates to an intraluminal sleeve system including active agents.

BACKGROUND

Intraluminal sleeves have a successful history of inducing weight loss in obese patients. The sleeve may be positioned in the intestine of the patient, covering portions of the duodenum and jejunum. The sleeve creates a barrier that prevents food processed in the patient's stomach from contacting walls of the patient's intestine. Consequently, the patient loses weight and if the patient is diabetic or has metabolic syndrome, diabetic and pre-diabetic symptoms may be diminished. In response, this causes the patient's metabolism to change, and causes the patient to more effectively process the food the patient ingests. These changes are likely the cause for the known "plateau" in a patient's rate of weight loss over time, even with the intraluminal sleeve in place.

Despite the relative safety and success of intraluminal sleeves in treating obesity and obesity related conditions, there remains a need for improved systems and methods for treating obesity and obesity related conditions in some patients.

SUMMARY OF THE INVENTION

The present invention provides an intraluminal sleeve system generally comprising an intraluminal sleeve configured to be placed in the intestine of a patient. Further, in embodiments of the present invention, the intraluminal sleeve is capable of dispensing an active agent, such as but not limited to, a metabolic agent, for example, a satiety inducing agent, to the patient while the intraluminal sleeve is positioned in the patient's intestine. The system may provide more effective obesity treatment relative to obesity treatment using an intraluminal sleeve alone.

In one embodiment, the present invention comprises an intraluminal sleeve including a reservoir configured to contain an active agent being effective, when released into the patient, to at least assist in effecting weight loss in the patient. The reservoir has an outlet configured to allow the active agent to exit the reservoir and contact a portion of the patient's body. A tube may be coupled to the reservoir to allow the active agent to be distributed to a desired portion of the patient's body.

In some embodiments of the invention, the satiety inducing agent is a hormone, for example, a peptide hormone. The peptide hormone may be at least one agent selected from a group comprising Glucagon-like peptide (GLP-1), Oxyntomodulin (OXM), Peptide YY (PYY), Pancreatic Polypeptide (PP), Insulin, Leptin, Gastrin, Ghrelin blocker, inhibitors of DPP-IV, and Amylin. The satiety inducing agent may be Cholecystokinin (CCK), which may suppress appetite when administered with or without gastric distension.

It is to be appreciated that the active agents useful in the present invention are not limited to satiety inducing agents but may also include any active agents, for example, other metabolic agents, that may provide some benefit to a patient suffering from obesity and/or obesity related conditions.

In one embodiment, the present invention comprises a method for the treatment of obesity, comprising the step of implanting an intraluminal sleeve into a patient's intestine. The intraluminal sleeve is configured to dispense an active agent to the patient that is effective, when released into the patient, to at least assist in effecting weight loss in the patient.

In one embodiment, the present invention comprises a system for the treatment of obesity including an intraluminal sleeve and an electrode coupled to the intraluminal sleeve, which is configured to apply electric stimulation to a portion of the patient's body.

In one embodiment, the present invention comprises a method for the treatment of obesity comprising the steps of inserting an electrode into a patient's body laparoscopically, and coupling the electrode to the lower third of the patient's esophagus. The electrode is configured to apply electric stimulation to the lower third of the patient's esophagus. The electrode is utilized in combination with an intraluminal sleeve positioned within the patient's intestine.

In one embodiment, an ancillary device is incorporated into the intraluminal sleeve and the ancillary device includes, or is capable of dispensing to the patient, a satiety inducing agent. The ancillary device may be structured to provide controlled release of the satiety inducing agent to the patient.

For example, the ancillary device may comprise a membrane or film permeable to a satiety inducing agent. The agent may be covered or enclosed by the membrane and is released into the body by diffusion through the membrane.

In one embodiment, the ancillary device may comprise a composition including a matrix material and a satiety inducing agent combined with the matrix material. The matrix material may be a biodegradable or bioerodible material, for example, a bioerodible polymer which, during erosion thereof in the body, releases the agent from the composition in a controlled manner.

In one embodiment, the ancillary device may be a non-bioerodible material. The device may include structures for containing and releasing the satiety inducing agents, for example, in a controlled manner. In one embodiment, the ancillary device includes recessions, pores or grooves capable of containing a satiety inducing agent.

In one embodiment, the ancillary device further includes a film or membrane in contact with the agent, and is capable of releasing the agent from the ancillary device and into the patient, for example, at a controlled rate.

In one embodiment, the intraluminal sleeve itself is structured to be capable of releasing a satiety inducing agent into the patient at a controlled rate.

In one embodiment, the present invention comprises an intraluminal sleeve system for the treatment of obesity comprising an intraluminal sleeve configured to be positioned in a patient's intestine, an implantable sensor coupled to the intraluminal sleeve and configured to sense a biological characteristic of the patient, and an external control device configured to receive a telemetric signal sent in response to the biological characteristic being sensed by the implantable sensor, and to produce a notification to perform an action effective to vary the biological characteristic sensed by the implantable sensor.

The biological characteristic may comprise a hormone level of the patient. The action may comprise injection of an active agent into the patient's body, inhaling of an active agent by the patient, drinking of an active agent by the patient, application of a patch to the patient's body being capable of distributing an active agent to the patient, spraying of an active agent into the patient's mouth, swallowing of a pill by the patient containing an active agent, insertion of a gum or film containing an active agent into the patient's mouth. A combination of actions may be taken, in response to the biological characteristic sensed by the sensor.

Each and every feature described herein, and each and every combination of two or more of such features, is included within the scope of the present invention provided that the features included in such a combination are not mutually inconsistent.

DETAILED DESCRIPTION

The present invention provides for intraluminal sleeve systems for the treatment of obesity, including intraluminal sleeves configured to be positioned within a patient's intestine. In embodiments of the present invention, the intraluminal sleeve system may be capable of dispensing an active agent to a portion of a patient's body. The active agent may be effective, when released into the patient, to at least assist in effecting weight loss in the patient. An embodiment of the intraluminal sleeve system that includes an active agent may provide more effective obesity treatment relative to obesity treatment using an intraluminal sleeve alone.

Figure 1:
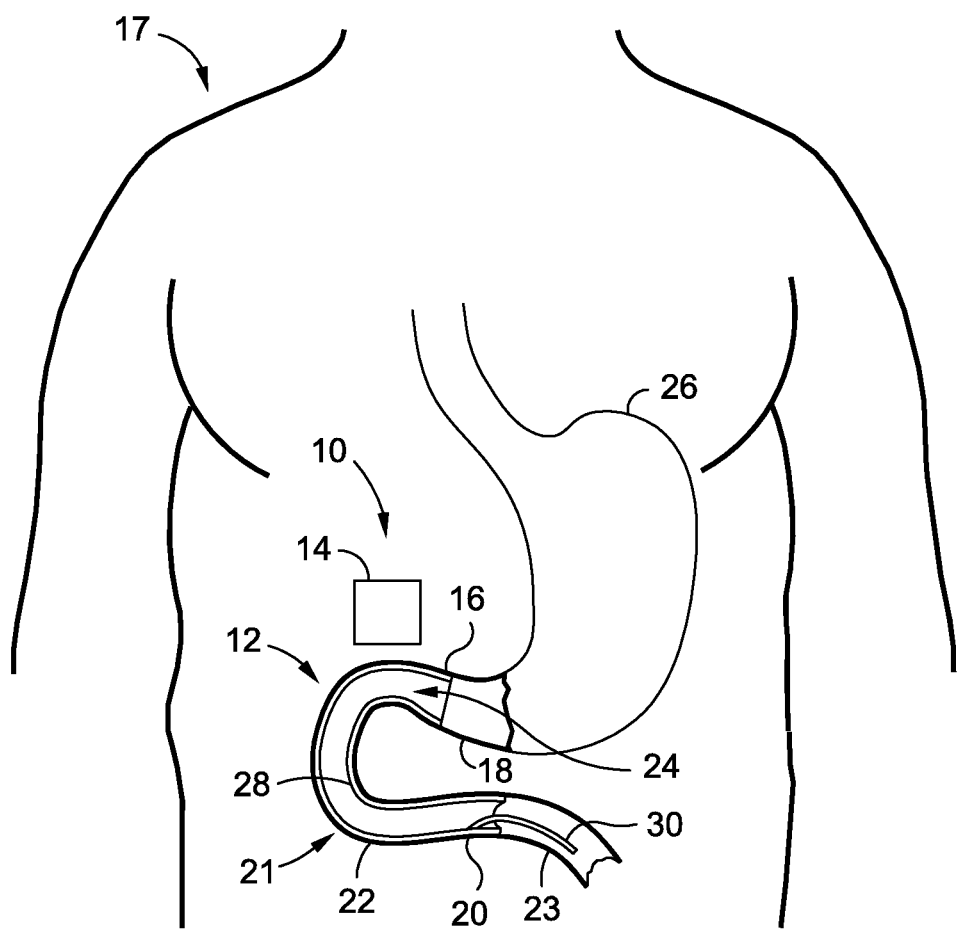
FIG. 1 is a perspective view of a system for the treatment of obesity according to one embodiment of the present invention.

FIG. 1 illustrates an embodiment of an intraluminal sleeve system 10 including an intraluminal sleeve 12 and a sensor 14. The intraluminal sleeve 12 comprises a sheath, or flexible cylinder positioned in the patient's small intestine 21. The intraluminal sleeve 12 has a first end 16 positioned in the patient's 17 duodenum 22, near the patient's pylorus 18. The intraluminal sleeve 12 has a second end 20 positioned in the patient's jejunum 23. The first end 16 comprises an open end of the flexible cylinder and the second end 20 similarly comprises an open end of the flexible cylinder. The open ends 16, 20 of the intraluminal sleeve 12 connect to form an interior lumen 24 of the intraluminal sleeve 12. The interior lumen 24 of the intraluminal sleeve 12 allows partially digested food, or chyme, produced in the patient's 17 stomach 26 to pass from the first end 16 of the intraluminal sleeve 12, and through the interior lumen 24, to exit the second end 20 of the intraluminal sleeve 12.

The intraluminal sleeve 12 serves as a barrier to prevent chyme, or other matter passing from the stomach, from contacting the walls of the patient's 17 small intestine 21 that the sleeve 12 covers. For example, as shown in FIG. 1, the intraluminal sleeve 12 may prevent chyme from contacting the patient's duodenum 22 and a portion of the jejunum 23. Isolating chyme from portions of the small intestine 21, including the intestinal epithelia tissue, may beneficially modify the patient's 17 metabolism, to control the rate at which the patient gains weight.

In the embodiment of the intraluminal sleeve 12 shown in FIG. 1, a reservoir 28 has been incorporated into the intraluminal sleeve 12. A tube 30 couples to the reservoir 28. A first end of the tube 30 couples to the reservoir 28 and a second end extends into a portion of the patient's small intestine 21, for example, the jejunum 23.

The reservoir 28 is configured to contain an active agent being effective, when released into the patient 17, to at least assist in effecting weight loss in the patient 17. The active agent may be a metabolic agent, for example, a satiety inducing agent, for example, a satiety gut hormone or bioactive molecule. Although the present disclosure will typically be discussing, specifically, satiety inducing agents, it is to be appreciated that the present invention, in all embodiments, is not limited to active agents that are, specifically, satiety inducing agents. Active agents useful with the present invention are intended to include other compositions, drugs or other agents, for example, agents that affect body metabolism without necessarily affecting satiety, that are believed to be effective, at least to some degree, in facilitating weight loss in a human being.

Figure 2:
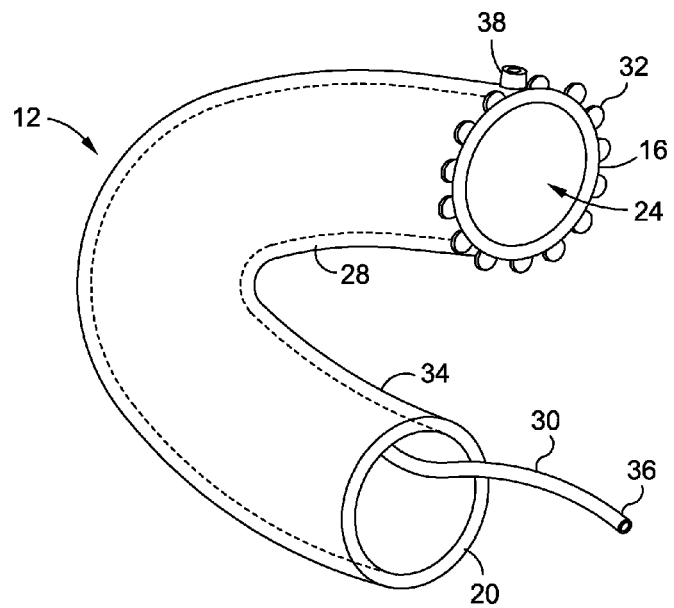
FIG. 2 is a perspective view of an intraluminal sleeve according to one embodiment of the present invention.

FIG. 2 illustrates a perspective view of the intraluminal sleeve 12 shown in FIG. 1. As discussed in relation to FIG. 1, the intraluminal sleeve 12 comprises a cylindrical sheath that prevents chyme from contacting portions of the patient's small intestine. The first end 16 of the intraluminal sleeve 12 includes an anchor device 32 for securing the first end 16 of the intraluminal sleeve 12 to a portion of the patient's small intestine 21. This portion may comprise the patient's duodenum 22, or the portion of the duodenum 22 near the patient's pylorus 18, as shown in FIG. 1. The anchor device 32 may comprise a flanged end of the intraluminal sleeve 12, which is sufficiently wide enough to be secured in place against the walls of the small intestine, including the duodenum 22. The anchor device 32 may additionally comprise a series of eyelets, which allow the first end 16 of the intraluminal sleeve 12 to be sutured or tacked in place against the walls of the small intestine 21. In one embodiment, the anchor device 32 may comprise an expandable wireframe, or any other device capable of securing the first end 16 of the intraluminal sleeve 12 to the small intestine 21. In one embodiment, the anchor device 32 may comprise sutures, tacks, staples, clips, hooks, adhesives, ports, or the like.

The first end 16 of the intraluminal sleeve 12 defines an opening of the sleeve 12 for chyme to enter the interior lumen 24 of the sleeve 12. The opening of the sleeve 12 may be structured and sized based on the shape of the anchor device 32. For example, if the anchor device 32 is shaped as a ring, then the opening of the first end 16 may be similarly shaped as a ring.

An outer surface 34 of the intraluminal sleeve 12 connects the first end 16 of the sleeve 12 to the second end 20 of the sleeve 12. The second end 20 of the sleeve 12 serves as an exit for the chyme that enters the first end 16 of the sleeve 12. The tube 30 exits the second end 20 of the intraluminal sleeve 12. A second end 36 of the tube 30 is capable of dispensing the active agent from the reservoir 28.

The reservoir 28 comprises a lumen positioned within the outer surface 34 of the intraluminal sleeve 12. The lumen of the reservoir 28 is positioned exterior to the interior lumen 24 of the intraluminal sleeve 12. The lumen of the reservoir 28 and the interior lumen 24 of the intraluminal sleeve 12 thus form a double lumen system, with the interior lumen 24 forming a passage for chyme to pass through the intraluminal sleeve 12, and the reservoir 28 forming a second lumen for containing an active agent. In the embodiment shown in FIG. 2, and as more clearly shown in FIG. 3, the reservoir 28 forms a cylindrically-shaped lumen around the interior lumen 24.

A fill valve 38 may be fluidly coupled to the reservoir 28. The fill valve 38 allows a physician to insert fluid, for example, an active agent into the reservoir 28 through appropriate means. For example, a physician may insert a filling mechanism, or filling tube, endoluminally through the patient's esophagus, and stomach, to engage the fill valve 38. The physician may fill the reservoir 28 with fluid, including an active agent, as desired. The fill valve 38 may comprise a one-way valve, or check valve, that does not permit the active agent to exit the reservoir 28 once it has entered the reservoir 28. The one-way valve may be configured as a leaf-valve, a duckbill valve, a diaphragm valve, or the like.

Figure 3:
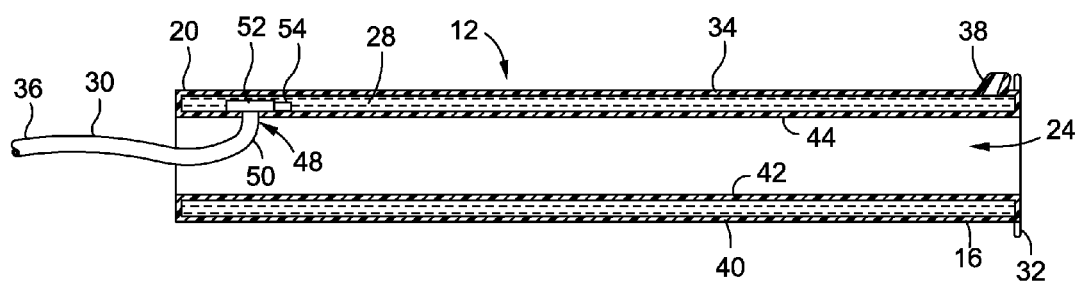
FIG. 3 is a side cross-sectional view of an intraluminal sleeve according to one embodiment of the present invention.

FIG. 3 illustrates a side cross-sectional view of the intraluminal sleeve 12 shown in FIGS. 1 and 2. The intraluminal sleeve 12 is shown to comprise a cylindrical sheath having an interior lumen 24 that allows chyme to pass therethrough. The interior lumen 24 is formed by an interior surface 44 of the intraluminal sleeve 12, which serves as a barrier for the chyme, to prevent the chyme from contacting the wall of the intestine. The lumen of the reservoir 28 encircles the interior lumen 24.

In the embodiment shown in FIG. 3, an outer wall 40 of the intraluminal sleeve 12 comprises the outer wall of the reservoir 28. The outer wall 40 of the intraluminal sleeve 12 also forms an outer surface 34 of the intraluminal sleeve 12, which contacts the walls of the patient's intestine. An inner wall 42 of the intraluminal sleeve 12 forms an inner wall of the reservoir 28. The embodiment of the intraluminal sleeve 12 shown in FIG. 3 is shaped substantially cylindrical, with a hollow center, with the outer wall 40 forming an outer wall of the cylinder, and the inner wall 42 forming an inner wall of the cylinder. The inner wall 42 and the outer wall 40 of the sleeve 12 therefore have substantially cylindrical shapes. The walls 40, 42 of the intraluminal sleeve 12 may be made from polytetrafluoroethylene, or any other material capable of producing equivalent operation.

In one embodiment, the intraluminal sleeve 12 may form a substantially tubular member configured to be positioned in the patient's intestine. In one embodiment, the intraluminal sleeve 12 may be shaped as a tapered cylinder, or a conical cylinder, or any other shape capable of producing equivalent operation.

The reservoir 28 comprises a chamber or housing capable of being filled with an active agent in fluid form. The reservoir 28 may include flexible outer walls, to accommodate the movement of the intraluminal sleeve 12 during implantation. In addition, the walls of the reservoir 28 may be capable of stretching, or expanding, to accommodate fluid being delivered into the reservoir 28. In one embodiment, the reservoir 28 may have a fixed size, and may not expand to accommodate fluid being delivered to the reservoir 28, yet may remain flexible, to accommodate the movement of the intraluminal sleeve 12 during implantation.

The reservoir 28 includes an outlet 48 that allows the active agent to exit the reservoir 28. The outlet 48 of the reservoir 28 may comprise a fluid channel or passageway that allows the active agent to pass from the reservoir 28 to contact a portion of the patient's body. In the embodiment shown in FIG. 3, the outlet 48 comprises an opening in the inner wall 42 of the intraluminal sleeve 12, which allows the active agent to pass from the reservoir 28 and dispense to the patient's body.

The tube 30 may couple to the outlet 48 of the reservoir 28. The tube 30 may comprise a tubular member, or fluid conduit, made, for example, from silicone or the like. One end 50 of the tube 30 may couple to the outlet 48 of the reservoir 28. The other end 36 of the tube 30 may be an open end, and may be positioned in a desired position within the patient's body, to allow the active agent to flow from the reservoir 28 and distribute to the desired portion of the patient's body. As shown in FIG. 1, for example, one end of the tube 30 may extend into the jejunum 23 of the patient's 17 body. The active agent may flow from the reservoir 28, through the tube 30, and be absorbed by the tissues of the intestine.

Referring back to FIG. 3, the outlet 48 may include an outlet device 52. The outlet device 52 may allow, enhance, prevent, or impede the ability of the active agent to exit from the reservoir 28. The outlet device 52 may be coupled to the intraluminal sleeve 12, in a position near the inner wall 42 of the intraluminal sleeve 12. The outlet device 52 may comprise a device selected from a group including a pump and a valve, or may comprise a combination of a pump and a valve. The pump and/or valve may be powered, either inductively from a remote device or through a battery (not shown) that may be charged prior to implantation of the intraluminal sleeve 12, or may be charged inductively after implantation, through appropriate means.

The pump may comprise a micro-pump, for example, a piezoelectric pump capable of driving fluid through use of a diaphragm mechanism. In addition, the pump may comprise any other desired type of implantable pump or micro-pump, capable of providing equivalent operation.

The valve may comprise a piezoelectric valve, for example, a valve capable of allowing fluid to pass through the outlet 48 with a powered diaphragm mechanism. The valve may also comprise any other desired type of valve device or micro-valve capable of providing equivalent operation. Embodiments of the pumps and/or the valves that may be preferably utilized in the present invention are disclosed and discussed in U.S. patent application Ser. No. 12/428,311, titled "Remotely Adjustable Gastric Banding System," filed Apr. 22, 2009, the entire disclosure of which is incorporated herein by reference.

The embodiments of the outlet device 52 that include the powered mechanisms (e.g., the pump and the valve) may be used in conjunction with a controller 54. The controller 54 may be coupled to the intraluminal sleeve 12 near the outlet device 52. The controller 54 may comprise circuitry and/or a power system capable of operating the outlet device 52 and communicating with other devices utilized in the intraluminal sleeve system 10. The controller 54 may include transmitter and receiver devices, which may send and receive signals telemetrically.

Figure 17:
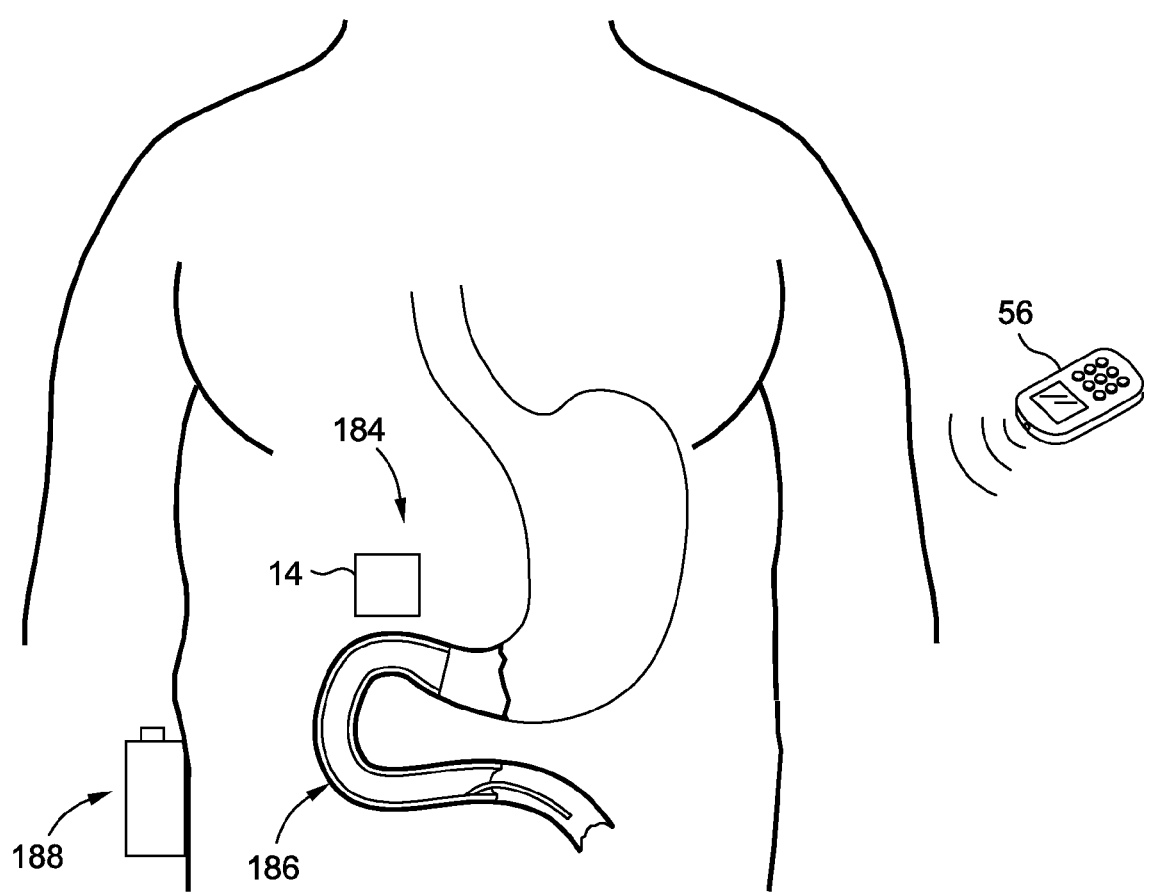
FIG. 17 is a perspective view of a system for the treatment of obesity according to one embodiment of the present invention.

The controller 54 may be capable of causing the outlet device 52 to increase a flow of active agent from the reservoir 28, or to decrease a flow of active agent from the reservoir 28, in response to signals sent by the sensor 14 (shown in FIG. 1) or an external controller device 56 (discussed in relation to FIG. 17). For example, the controller 54 may cause an embodiment of the outlet device 52 comprising a pump, to pump active agent from the reservoir 28 in response to a signal sent from the sensor 14. In addition, the controller 54 may be configured to open or close an embodiment of the outlet device 52 comprising a powered valve, in response to a signal sent from the sensor 14.

The receiver of the controller 54 may include an antenna, capable of receiving signals transmitted from inside the body or outside the body. If signals are transmitted from inside the body, the signals may be sent from the sensor 14 (shown in FIG. 1), which may be configured to wirelessly transmit signals to the controller 54. If signals are transmitted from outside the body, the signals may be sent from an external control device 56 (discussed in relation to FIG. 17). Both the sensor 14 and the external control device 56 may be capable of transmitting signals to the controller 54. The transmitted signals may cause the controller 56 to increase or decrease the rate the active agent exits the reservoir 28. For example, the transmitted signals may instruct the outlet device 52 to pump an active agent through the outlet 48, or pump less of the active agent through the outlet 48, or to open or close a powered valve incorporated with the outlet device 52. The controller 54 may be powered by similar means as the outlet device 52, namely, through battery power or through induction.

The transmitter of the controller 54 may include an antenna, which may be the same antenna as used with the receiver, and is capable of transmitting signals outside the body. The transmitted signals may be utilized in various embodiments of the intraluminal sleeve system. For example, in one embodiment, the controller 54 may include a flow meter, and the transmitter may be capable of sending a signal to a physician, indicating whether a certain amount of active agent has passed through the outlet 48. In one embodiment, the controller 54 may detect whether the pump is operating, or the valve is open. In this embodiment, the transmitter may alert a physician when the active agent is being distributed from the reservoir 28.

In one embodiment, a pressure sensor may be incorporated with the reservoir 28, capable of signaling to the controller 54 when the pressure level of the reservoir 28 is low enough to require more active agent to be inserted into the reservoir 28, or to require the intraluminal sleeve 12 to be replaced. The transmitter may send a signal to an external control device 56 (discussed in relation to FIG. 17), indicating a fluid level or volume of the reservoir 28 to the user of the external control device 56.

In one embodiment, the controller 54 may include a processor and a memory, the memory being capable of storing instructions executable by the processor. The instructions may be preprogrammed into the controller 54 prior to implantation of the intraluminal sleeve 12, or may be received by the receiver of the controller 54, and set into the memory by the patient or physician wirelessly, after implantation. The instructions may produce any of the actions performed by the controller 54.

Referring back to FIG. 1, the system 10 may further include a biological sensor 14 which may be utilized in combination with the reservoir 28. The sensor 14 may comprise circuitry including a biological sensor capable of detecting a desired biological characteristic, property, or value. The biological characteristic may be a hormone level, which may be detected through means known to those skilled in the art. For example, a hormone level of the patient may be measured by measuring the dielectric constant of interstitial fluid, intra-peritoneal fluid, or blood plasma, across two electrodes, in a manner that reflects the hormone concentration of the patient. The sensor 14 may include a receiver and a transmitter, which are respectively capable of receiving and sending signals to the controller 54 of the reservoir 28 (shown in FIG. 3), or to a receiver located exterior to the patient's body.

The sensor 14 may be configured to cause a signal to be sent to the controller 54 (shown in FIG. 3) or an external control device 56 (shown in FIG. 17), in response to the measured biological characteristic of the patient. For example, the sensor 14 may be configured to store a threshold detection level for a biological characteristic within a patient's body. If the detected biological characteristic decreases below the threshold value, then the sensor may be configured to send a signal to the controller 54 of the reservoir 28 or to the external control device 56. The signal received by the controller 54 may cause the controller 54 to instruct, control, or power, the outlet device 52 to vary a rate the active agent is dispensed from the reservoir 28 and delivered to a portion of the patient's body. In this embodiment, the signal will preferably increase the rate the active agent is dispensed from the reservoir 28. In addition, or alternatively, a threshold detection level may be stored or set in the sensor 14 that represents an upper limit of a detected biological characteristic. For example, if the sensor 14 detects that the biological characteristic is above a threshold level, then the sensor 14 may send a signal to the controller 54 to instruct, control, or power, the outlet device 52 to reduce the amount of active agent being dispensed from the reservoir 28. The sensor 14 and the reservoir 28 may thus act in a closed feedback loop, which allows the amount of fluid dispensed from the reservoir 28 to be controlled, at least in part, by a biological characteristic of the patient's body. If the biological characteristic is a hormone level, the sensor 14 and the reservoir 28 may then act in a feedback loop to control the hormone level of the patient. The sensor 14 may be powered, inductively from a remote device or through a battery (not shown) that may be charged prior to implantation of the intraluminal sleeve system 10, or charged inductively after implantation, through appropriate means.

In one embodiment, the sensor 14 may include a processor and a memory. The processor may be capable of executing instructions stored in the memory. The instructions may be preprogrammed into the sensor 14 prior to implantation, or may be received by the sensor and set into the memory by the patient or physician wirelessly, after implantation. The instructions may comprise any of the actions and responses performed by the sensor 14. For example, the instructions may include the threshold detection values set to be detected by the sensor 14.

The active agent that is dispensed from the reservoir 28 may comprise an active agent that is a satiety inducing agent. The satiety inducing agent may be a hormone, for example, a peptide hormone. The hormone may comprise at least one agent selected from a group comprising Glucagon-like peptide (GLP-1), Oxyntomodulin (OXM), Peptide YY (PYY) and Peptide YY (3-36) (PYY (3-36)), Pancreatic Polypeptide (PP), Insulin, Leptin, Gastrin, Ghrelin blocker, inhibitors of DPP-IV, and Amylin. In addition, the satiety inducing agent may be Cholecystokinin (CCK) or Cholecystokinin 8 (CCK-8) or Pro-opiomelanocortin (POMC), or others, or any combination of the above.

The active agent may also be an agent selected from a list of agents comprising Glial-Derived Neurotrophic Factor (GDNF); Serotonin; Dopamine and its Analogues such as: Ibogaine, Noribogaine, 18-MC, and Cabergoline; Ciliary-derived Neurotrophic Factor (CNTF); Cocaine-Amphetamine Regulated Transcript (CART); Serotonin and its Analogues; Gastric Inhibitory Peptide or Glucose-dependant Insulinotropic Peptide (GIP); Neuropeptide Y (NPY) receptor antagonists and iRNA/siRNA; Orexin A and B receptor antagonists and iRNA/siRNA; Agouti Related Peptide (AgRP) receptor antagonists and iRNA/siRNA; Cannabanoid receptor antagonists and iRNA/siRNA; the Melanocortins: Pro-Opiomelanocortin (POMC), Alpha and Beta Melanocyte Stimulating Hormone ($\alpha$ and $\beta$ MSH); Melanin Concentrating Hormone (MCH) receptor antagonists and iRNA/siRNA; Adenosine Mono-Phosphate activated protein Kinase (AMPK); 5-aminoimidazole-4-carboxamide-1-$\beta$-D-ribofuranoside (AICAR); and Peroxisome Proliferator-Activated Receptor Delta Agonist (PPAR$\delta$-agonist), or others, or any combination of the above.

Discussions of gastrointestinal hormones that control appetite can be found in Chaudhri. O. B., Wynne, K., and Bloom, S. R. 2008. "Can Gut Hormones Control Appetite and Prevent Obesity?". Diabetes Care 31 (Suppl. 2): s284-s289. Additional information can be found in Cummings, David E. and Overduin, J. 2007. "Gastrointestinal Regulation of Food Intake." J. Clin. Invest. 117: 13-23, the entire disclosures of which are incorporated herein by reference. In the publication, "Can Gut Hormones Control Appetite and Prevent Obesity?" by Chaudhri, et al, research conducted on Gherlin, GLP-1, Oxyntomodulin, Inhibitors of DPP-IV, Amylin, Peptide YY, and Pancreatic Polypeptide to control appetite, are described. These as well as other hormones may be useful in accordance with the present invention. Similarly, "Gastrointestinal Regulation of Food Intake" by David E. Cummings et al. describes the efficacy of satiety hormones to boost weight loss.

In other embodiments of the invention, the active agent may be any suitable active agent that will improve the weight-loss effect of the intraluminal sleeve. For example, the active agent may be an agent that affects metabolism of a patient independently of the effect, if any, on satiety of the patient. The metabolic agents that are known or suspected to have a positive effect on weight loss are known to those of skill in the art.

In one embodiment, the active agent may be contained within microspheres that are held within the reservoir 28, or any other embodiment of a reservoir discussed in this application. The microspheres would be held in solution within the reservoir. The microspheres may be dispensed into the patient's body to release the active agent contained within the microspheres.

Any of the active agents discussed throughout this application may be bioengineered to resist the breakdown of the active agent. For example, in an embodiment, in which the active agent comprises a hormone, enzymes within a patient's body will begin a process of breaking down and rendering the hormone ineffective after the hormone is introduced into the patient's body. The enzymes target specific sites, particularly amino acids of the hormone, to cleave the hormone molecule, thus inactivating the hormone by changing its ability to bind to its receptor or exert its intended effect. To prevent this undesirable result, specific DNA capable of producing the hormone may be identified and modified to reduce the enzymatic degradation. For example, once a specific DNA sequence has been isolated and identified for the hormone of interest, small changes can be made to the DNA coding sequence. By altering the amino acid that is expressed following post-translational processing, insignificant changes can be made to the hormone molecule's stereo-structure while making the hormone relatively resistant to enzymatic degradation, thereby extending its half-life and efficacy. Methods of producing recombinant DNA are discussed in "AN INTRODUCTION TO GENETIC ANALYSIS" by Anthony Griffiths, Jeffery Miller, David Suzuki, Richard Lewontin, and William Gelbert, the entirety of which is incorporated by reference herein. Further information may also be found in "MOLECULAR CELL BIOLOGY" by Harvey Lodish, Arnold Berk, Paul Matsudaira, Chris Kaiser, Monty Krieger, Matthew Scott, S. Lawrence Zipursky, and James Darnell, the entirety of which is incorporated by reference herein.

In one embodiment, a Phenylethylene glycol (PEG) group may be added to any of the active agents discussed throughout this application, to enhance the effectiveness and longevity of the agent.

Referring back to FIG. 1, the intraluminal sleeve 12 is implanted into the patient's 17 intestinal system endoluminally. The intraluminal sleeve 12 is passed through the patient's 17 esophagus in a deflated state, in which no active agent, or a minimal amount of active agent is present in the reservoir 28. A wire-guided catheter system may be used to position the intraluminal sleeve 12 in the patient's intestine. The second end 20 of the intraluminal sleeve 12 may be placed in the desired position in the patient's intestine, and then the first end 16 of the sleeve 12, including the anchor device 32 (shown in FIG. 2), may be placed in the desired position in the patient's intestines. After the intraluminal sleeve 12 is in position, a filling mechanism (not shown) then engages the fill valve 38 (shown in FIG. 2) and fills the reservoir 28 with a desired volume of active agent. The filling mechanism may then be withdrawn from the patient's 17 stomach 26. In an embodiment in which the intraluminal sleeve 12 includes a tube 30, the tube 30 may be positioned in a desired position within the patient's 17 body. For example, one end of the tube 30 may be positioned in the patient's 17 jejunum 23. The tube 30 may be positioned through appropriate endoluminal means.

The sensor 14 of the intraluminal sleeve system 10 may be positioned laparoscopically within the patient's body in a desired position. Such positions may include locations in which the sensor 14 may detect interstitial fluid, intra-peritoneal fluid, or blood plasma, across two electrodes, in a manner that reflects the hormone concentration of the patient. For example, the sensor 14 may be positioned near highly vascularized and permeable tissue such as a mucous or serous membrane within the patient's body. In one embodiment, the sensor 14 may be positioned endoluminally within the patient's body. In this embodiment, the sensor 14 may be placed within the patient's stomach, or gastrointestinal tract. In one embodiment, the sensor 14 may be integrated as a component of the intraluminal sleeve 12. In this embodiment, the sensor 14 may be coupled to the intraluminal sleeve 12, and positioned along the intraluminal sleeve 12 to measure a local biological characteristic.

Once the intraluminal sleeve 12 is positioned within the patient's 17 intestines, the reservoir 28 acts to dispense the active agent to the patient's 17 body, and does so in combination with the intraluminal sleeve 12 that serves as a barrier to chyme passing through the sleeve 12. The use of the reservoir 28 thus serves to enhance the therapeutic properties of the intraluminal sleeve 12 treatment, by distributing an active agent that promotes satiety signals of the patient, or alters the metabolism of the patient, both of which are intended to cause the patient to lose weight.

The dosage of the active agent that is distributed by the reservoir 28 may be adjusted by a physician to accommodate various personal properties of the patient (e.g., weight loss goal, size of the patient, results of the intraluminal sleeve device and active agent treatment). For example, a physician may communicate with the sensor 14 to set a certain biological threshold detection level (e.g., a hormone threshold detection level), which corresponds to the personal properties of the patient. The sensor 14 may send a signal to the controller 54 (shown in FIG. 3) or an external control device 56 (shown in FIG. 17) if a measured biological characteristic deviates from the threshold detection level. In addition, a physician may communicate with the reservoir 28, via the controller 54, to set a degree of flow and volume from the reservoir 28, or to set a pumping or flow rate of the outlet device 52, according to the personal properties of the patient. In addition, the physician may program in the controller 54, a schedule at which the active agent is dispensed from the reservoir 28.

In the embodiment shown in FIG. 1, the intraluminal sleeve 12 has one end 16 positioned in the duodenum 22 of the patient and another end 20 positioned in the jejunum 23. However, the length and position of the intraluminal sleeve 12 may be varied as desired. In one embodiment, the intraluminal sleeve may extend for approximately twenty inches, and may extend into the jejunum 23, as shown in FIG. 1. In one embodiment, the intraluminal sleeve may have a length of approximately nine inches, and may only cover a portion of the duodenum 22. In various embodiments, the length of the intraluminal sleeve may be varied as desired. The second end 20 of the intraluminal sleeve may terminate in the proximal small intestine, or the distal small intestine. Further, in one embodiment, the first end 16 of the intraluminal sleeve may be located in varied positions in the patient's body, including in the patient's stomach, in the pylorus, or further down the duodenum than shown in FIG. 1. In one embodiment, the outside diameter of the intraluminal sleeve may be close in size to the interior diameter of the small intestine.

In one embodiment, a portion of the intraluminal sleeve may be positioned in the patient's stomach, and may serve as a restriction member. Due to the intraluminal sleeve's restrictive properties, the sleeve may limit the volume of food that can be consumed at one time, and may expedite the activation of the stomach's stretch receptors. Such a sleeve may include a funnel at one end of the sleeve, to facilitate entry of food into the sleeve. Further, in one embodiment, the intraluminal sleeve may be used in conjunction with a gastric band. The sleeve is placed through the luminal opening of the gastric band, and a funnel at one end of the sleeve acts as a flange to hold the sleeve in place. In one embodiment, an intraluminal sleeve may be fixed within the stomach of a patient with sutures, tacks, staples, clips, hooks, adhesives, ports, or the like.

Referring back to FIG. 3, in one embodiment, the output device 52 comprises a check valve, or one-way valve, that is configured to allow an active agent to flow from the reservoir 28 in response to a force being exerted against the reservoir 28. The force may exert against the reservoir 28 by chyme passing through the interior lumen 24 of the intraluminal sleeve 12. The chyme may press against the inner wall 42, or inner surface 44, of the intraluminal sleeve 12, and pressurize the reservoir 28, to cause the one-way valve to open and dispense the active agent. The one-way valve may thus have a set pressure threshold, at, or above which, the one-way valve opens and allows fluid to pass through. The one-way valve may then be capable of beneficially distributing the active agent during times when the patient is eating or digesting (e.g., at times chyme presses against the reservoir 28). The active agent may then be dispensed at a time when increased satiety signals would be more useful to reduce the volume of food consumed by the patient. In one embodiment, the one-way valve may also be a variable one-way valve, or a one-way valve that is capable of varying the pressure the valve opens in response to. The opening pressure of the one-way valve may be varied by the physician mechanically, prior to implantation of the intraluminal sleeve 12, or mechanically after implantation of the intraluminal sleeve 12. In one embodiment, the one-way valve may operate in combination with the controller 54, and a physician may communicate wirelessly with the controller 54, to adjust the threshold pressure of the one-way valve.

Figure 4:
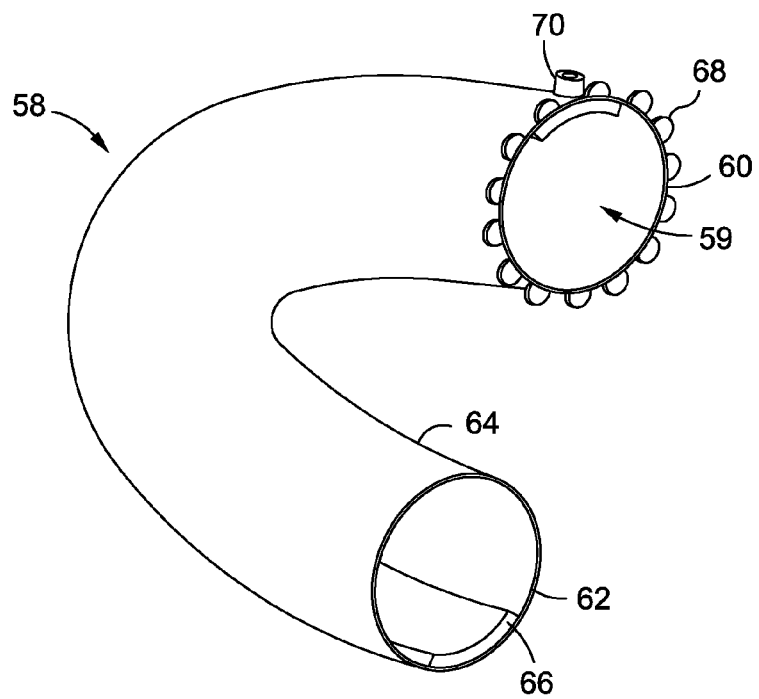
FIG. 4 is a perspective view of an intraluminal sleeve according to one embodiment of the present invention.

FIG. 4 illustrates an embodiment of an intraluminal sleeve 58 in which the reservoir 66 comprises only a portion of an inner surface of the sleeve 58 and an outer wall of the sleeve 58. The intraluminal sleeve 58 includes a first end 60 and a second end 62, with an interior lumen 59 connecting the two ends 60, 62. An outer surface 64 of the intraluminal sleeve 58 contacts the walls of the patient's small intestines. An anchor device 68, which may be configured similarly to the anchor device 32 discussed in relations to FIG. 2, is coupled to the first end 60 of the intraluminal sleeve 58. A fill valve 70, which may be configured similarly to the fill valve 38 discussed in relations to FIG. 2, is fluidly coupled to the reservoir 66.

Figure 5:
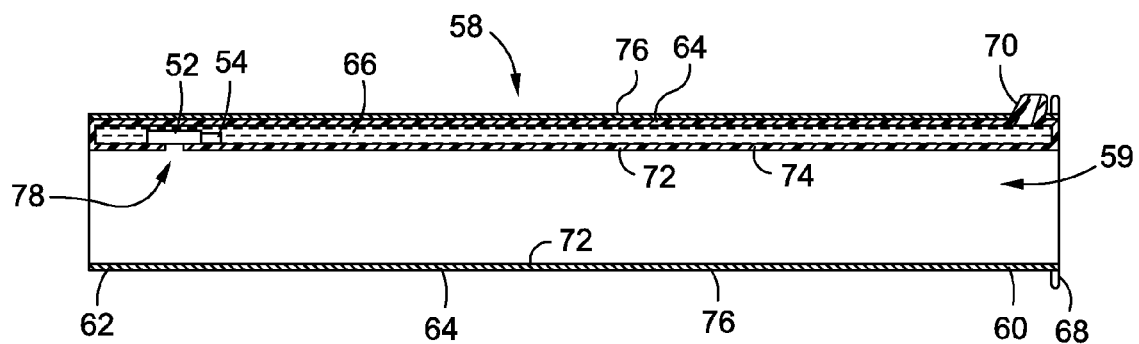
FIG. 5 is a side cross-sectional view of an intraluminal sleeve according to one embodiment of the present invention.

FIG. 5 illustrates a side cross-sectional view of the intraluminal sleeve 58 shown in FIG. 4. An outer wall of the reservoir 66 forms a portion of an outer wall 76 of the intraluminal sleeve 58. An inner wall of the reservoir 66 forms a portion of an inner wall 74 of the intraluminal sleeve 58. Thus, the inner wall of the reservoir 66 does not form the entire inner surface 72 of the intraluminal sleeve 58.

The outlet device 52 and the controller 54 shown in FIG. 5 may be configured similarly to the outlet device 52 and the controller 54 shown in FIG. 3.

In the embodiment shown in FIGS. 4 and 5, the intraluminal sleeve 58 does not include a tube, such as a tube 30 shown in FIG. 2, leading from the reservoir 66 to a portion of the patient's body. In this embodiment, the active agent may pass from the reservoir 66 directly to the patient's intestine, from the outlet 78 of the reservoir 28. A tube may or may not be utilized throughout all embodiments of the intragastric sleeves discussed throughout this disclosure.

Figure 6:
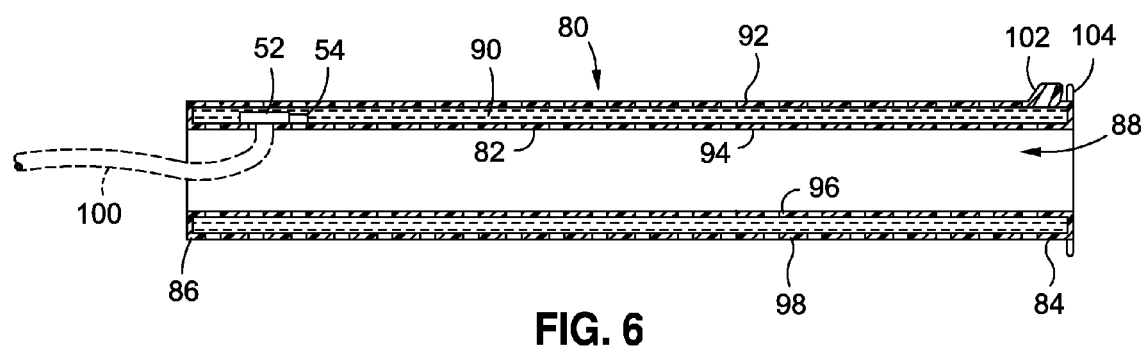
FIG. 6 is a side cross-sectional view of an intraluminal sleeve according to one embodiment of the present invention.

FIG. 6 illustrates an embodiment of an intraluminal sleeve 80 including a semi-permeable membrane 82. The semi-permeable membrane 82 comprises the outer surfaces of the reservoir 90, and forms the outer surface 92 of the intraluminal sleeve 80 and the inner surface 94 of the intraluminal sleeve 80. The semi-permeable membrane 82 also comprises the outer wall 98 and the inner wall 96 of the intraluminal sleeve 80. The intraluminal sleeve 80 has a first end 84 and a second end 86, and an interior lumen 88 passing between the ends 84, 86 of the intraluminal sleeve 80. An anchor device 104, which may be configured similarly as the anchor device 32 discussed in relation to FIG. 2, is coupled to the first end 84 of the intraluminal sleeve 80. A fill valve 102, which may be configured similarly as the fill valve 38 discussed in relation to FIGS. 2 and 3, is fluidly coupled to the reservoir 90. The outlet device 52 and the controller 54 shown in FIG. 6 may be configured similarly as the outlet device 52 and the controller 54 shown in FIG. 3.

The semi-permeable membrane 82 may comprise a silicone or nanostructure material capable of selectively diffusing the active agent through the membrane 82. The membrane 82 serves as an outlet for the reservoir 90, allowing the active agent to diffuse through the membrane 82 based on a concentration difference, or mass action, of the active agent on one side of the membrane 82, in relation to the concentration on the other side of the membrane 82.

In the embodiment shown in FIG. 6, the semi-permeable membrane 82 may be configured to contact a portion of the patient's intestine and allow the active agent to diffuse into the local tissues within the patient's intestine. Although the active agent may diffuse through the semi-permeable membrane 82, an outlet device 52 and/or a controller 54 may be used to enhance the flow of the active agent to exit the reservoir 90.

In the embodiment shown in FIG. 6, a portion of a tube 100 extending from the reservoir 90 includes a semi-permeable membrane. The active agent may diffuse from the tube 100 as the active agent passes through the tube 100, to be dispensed to a portion of the patient's body. In addition, in one embodiment, one end of the tube 100 may be closed, such that the active agent can not pass through the closed end of the tube 100. Rather, the active agent may only exit the tube 100 through the semi-permeable membrane. The tube 100 may be positioned as desired, for example, in the patient's upper intestines, and the active agent may slowly diffuse through the membrane of the tube 100, and into the local tissues of the upper intestines. In this embodiment, the semi-permeable membrane of the tube comprises the outlet of the reservoir 90.

Figure 7:
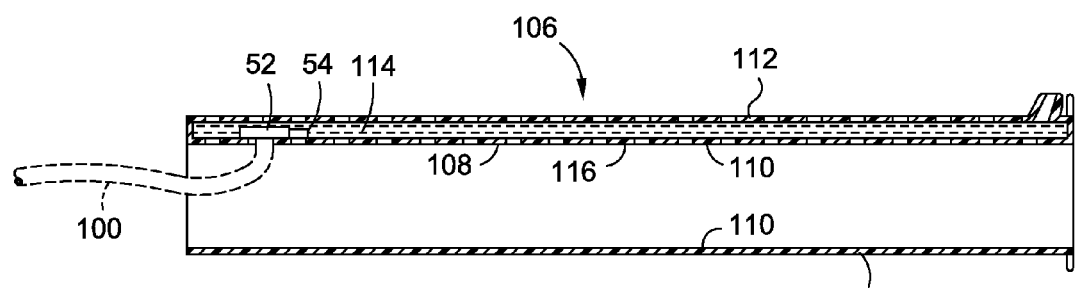
FIG. 7 is a side cross-sectional view of an intraluminal sleeve according to one embodiment of the present invention.

FIG. 7 illustrates an embodiment of an intraluminal sleeve 106 in which a semi-permeable membrane 108 only forms a portion of an inner surface 110 of the sleeve 106 and an outer wall 112 of the sleeve 58. An inner wall of the reservoir 114 forms a portion of an inner wall 116 of the intraluminal sleeve 106. Thus, the inner wall of the reservoir 114 does not form the entire inner surface 110 of the intraluminal sleeve 106. The semi-permeable membrane 108 thus only forms a portion of the intraluminal sleeve 106.

Figure 8:
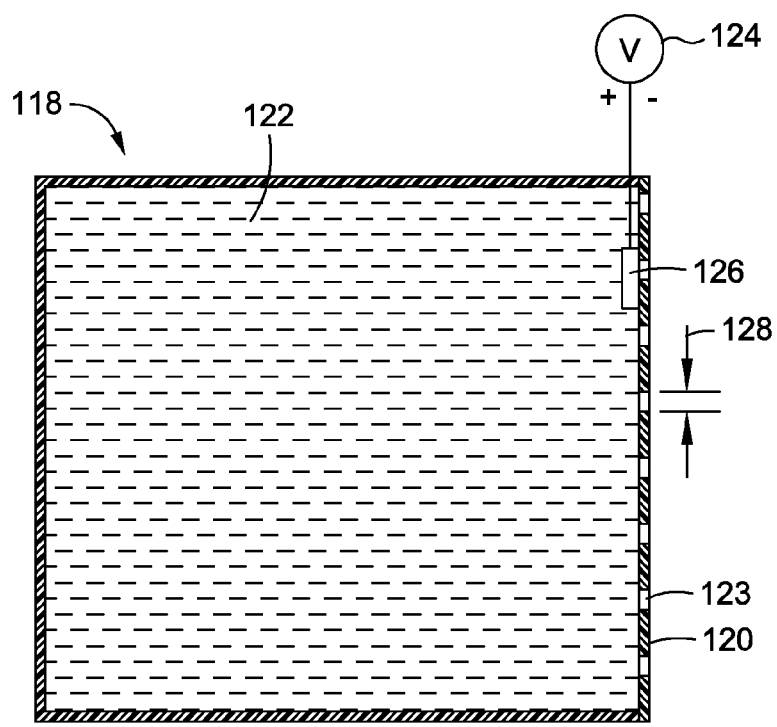
FIG. 8 is a schematic view of a reservoir according to one embodiment of the present invention.

FIG. 8 illustrates a schematic representation of a reservoir 118 having a semi-permeable membrane 120. The reservoir 118 may represent any of the reservoirs discussed in relation to FIGS. 6-7, or any portion of an intraluminal sleeve system having a semi-permeable membrane. The reservoir 118 includes a central chamber or housing, configured to contain an active agent 122, represented by dashed lines in FIG. 8. An outer surface of the reservoir 118 comprises a semi-permeable membrane 120, having a series of pores 123 for the active agent 122 to pass through and exit the reservoir 122. The active agent 122 may diffuse through the semi-permeable membrane 120 based on a diffusive force, caused by a concentration differential of the active agent 122 on one side of the membrane 120 in relation to the other side of the membrane 120. The rate of diffusion may depend in part on the porosity of the membrane 120, the diffusibility of the active agent across the surface of the membrane 120, and the surface area to volume ratio of the reservoir 118. Such design features of the reservoir 118 may be varied to produce a desired effect.

In one embodiment, the passage of the active agent 122 from one side of the membrane to the other may be aided or hindered by use of a voltage source 124 and an electrode 126, utilized in combination with the reservoir 118. The voltage source 124 may be powered, either inductively from a remote device or through a battery (not shown) that may be charged prior to implantation of the implantable system or charged inductively after implantation, through appropriate means. The electrode 126 may be positioned on either side of the membrane 120, or on both sides of the membrane 120, or generally within the reservoir 118 as desired. The voltage source 124 and the electrode 126 operate to form an electric charge on one side of the membrane 120, or on both sides of the membrane 120. The charge may enhance or impede the diffusion of the active agent from the reservoir 118 to the patient's body, as the active agent 122 may comprise molecules having a net charge, or a polarity. Based on the charge of the molecules forming the active agent, the electrode 126 may cause a charge to be formed on either side of the membrane 120 that either draws the active agent 122 out from the reservoir 118, or serves to keep the active agent 122 within the reservoir 118, through an electric force.

The desired polarity of the charge formed on either side of the membrane 120 will depend on the polarity of the molecules that were selected to comprise the active agent 122. In one embodiment, the net charge formed by the electrode 126 on either side of the membrane 120 may be varied as desired by the voltage source 124. In this embodiment, the voltage source 124 may be a variable voltage source. The voltage output by the voltage source 124, and the polarity of the net charge formed by the voltage source 124, may be controlled by, for example, the controller 54 discussed in relation to FIGS. 3, 5, 6 and 7. The controller 54 may be appropriately configured to instruct the voltage source 124 to produce a charge in response to a signal from the sensor 14 (shown in FIG. 1), or the external control device 56 (shown in FIG. 17). For example, the controller 54 may receive a signal from the sensor 14, directing the voltage source 124 to increase or decrease the strength, or polarity, of the net charge formed on either side of the membrane 120. If the sensor 14 detects a low hormone level in the patient, the sensor 14 may send a signal to the controller 54 instructing the controller 54 to increase the flow of the active agent 122 through the membrane 120. The controller 54 may instruct the voltage source 124 to increase the net charge, or vary the polarity of the charge, on one side of the membrane 120, if such an action will increase the flow of the active agent 122 through the membrane 120. A signal received from the external control device 56 may produce a similar result.

In one embodiment, the controller 54 may be configured to control the voltage source 124 to increase or decrease the strength or polarity of the net charge formed on either side of the membrane 120, according to a schedule. The controller 54 may be pre-programmed with a control schedule that defines the times the voltage source 124 will enhance or impede diffusion of the active agent 122 through the membrane 120. The control schedule may be configured to enhance or impede the diffusion of the active agent 122 through the membrane 120 at specified times during the day. For example, the control schedule may include a schedule of meal times. The amount of active agent 122 dispensed may increase at the defined meal times. In addition, the control schedule may be set to reduce the flow of active agent 122 from the reservoir 118 during times when food consumption is not likely, for example, during times when the patient is likely to be sleeping. The control schedule may be configured to be varied or reprogrammed telemetrically after the controller 54 has been implanted. The control device 56, discussed in relation to FIG. 17, may be used to reprogram the controller 54.

In one embodiment, a pressure sensor may be incorporated with the reservoir 118. The pressure sensor may be capable of detecting a force exerted against the reservoir 118 by chyme passing through the intraluminal sleeve. The pressure sensor may send a signal to the voltage source 124 to increase the flow of active agent 122 through the membrane 120 in response to the force applied to the reservoir 122.

The response of the voltage source 124 to a signal from the sensor 14 (shown in FIG. 1), or external control device 56 (shown in FIG. 17), or pressure sensor, may be varied as desired (e.g., the voltage source 124 may decrease the net charge on one side of the membrane 120, if doing so would increase flow of the active agent 122 through the membrane 120). In one embodiment, the electrode 126 may equivalently comprise a plurality of electrodes, positioned throughout, and/or external to the reservoir 118, if equivalent operation results.

In one embodiment, the voltage source 124 and electrode 126 may be utilized to vary the size 128 of the pores 123 of the membrane 120. The membrane 120 may be made of a material structured to contract or expand in response to an electric voltage applied to the membrane 120. The material of the membrane 120 is composed such that the pore size 128 depends on the voltage being applied to the membrane 120, for example, the material may comprise an electroactive polymer having a series of pores. The size 128 of the pores 123 depends on the presence of a voltage applied by the electrode 126, which may either increase or decrease the size 128 of the pores 123. The active agent 122 may either more easily or less easily flow, through the membrane 120, if a voltage is applied to the membrane 120 by the electrode 126. In one embodiment, the voltage source 124 may be a variable voltage source 124, and may be controlled by the controller 54 discussed in relations to FIGS. 3, 5, 6 and 7. The controller 54 may operate in response to a signal produced by the sensor 14 (shown in FIG. 1) or an external control device 56 (shown in FIG. 17). For example, if the sensor 14 detects a low hormone level in the patient, the voltage source 124 may appropriately increase or decrease the voltage applied to the membrane 120, to increase the pore size 128, and increase the flow of the active agent 122 from the reservoir 118.

In one embodiment, the semi-permeable membrane 120 may be configured to vary the pore size 128 without the use of the voltage source 124 and the electrode 126. In this embodiment, the semi-permeable membrane 120 may be made from a material that varies in pore size 128 automatically in response to an environmental condition, based on the material properties of the membrane 120. The material may comprise polyethylene, or polyethylene filled with $SiO_2$. Such desirable materials are discussed in the publication, "Response of Filled Polyethylene Membranes to the Changes in the Environmental Conditions," M. A. Islam and N. D. Nikolov, volume forty-five, issue 8, Journal of Applied Polymer Science, the entirety of which is incorporated by reference. The environmental condition may comprise a biological property, for example, a pH level, a temperature, or an internal pressure of the patient. The material of the membrane 120 may be selected such that the pore size 128 will automatically adjust in response to the environmental condition, and will adjust to a desired degree in response to the environmental condition. Thus, for example, if a pH level in a certain level is present within a response range of the membrane 120, the pore size 128 may increase or decrease to vary the flow of the active agent 122, as desired.

Figure 9:
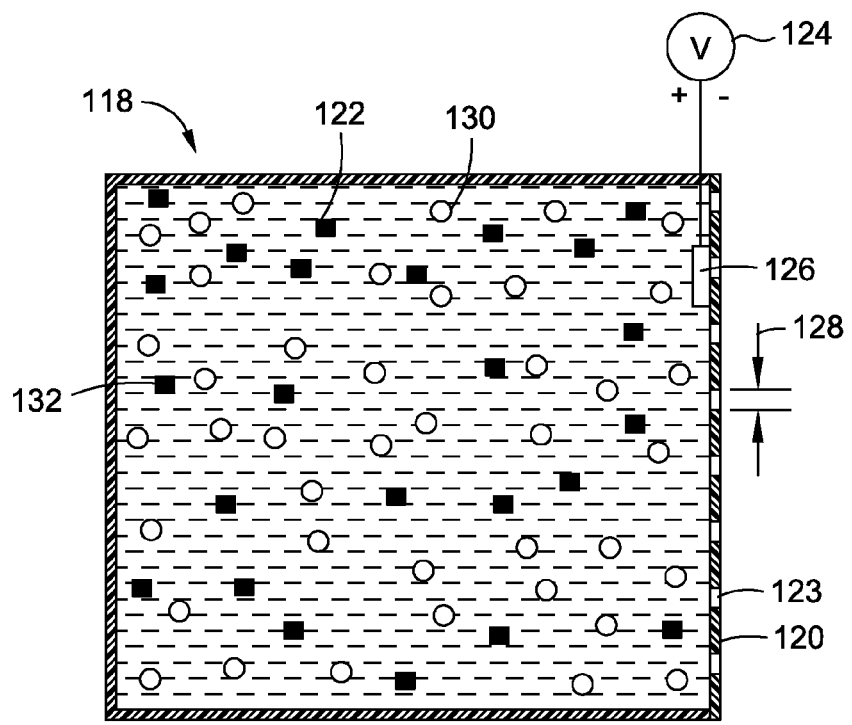
FIG. 9 is a schematic view of a reservoir according to one embodiment of the present invention.

FIG. 9 illustrates an embodiment of the reservoir 118 shown in FIG. 8, which utilizes the biological organisms 130 to produce the active agent 122. The biological organisms 130 are represented in FIG. 9 as circles, and may comprise any biological organism, preferably at the size of a microbe, or as would otherwise fit into the reservoir 118 for implantation within a patient's body. The organisms 130 may preferably comprise any cell or combination of zoograph cells, autograph cells, autograph cells, bacterium, algae, or yeast. The organisms 130 are stored within the reservoir 118 and are sustained by a nutrient media 132, represented in FIG. 9 as squares. The reservoir 118 is configured in a manner to properly store and keep the organisms 130 alive for an extended period of time. For example, the pores 128 are sized such that the organisms 130 cannot pass through the membrane 120, yet the active agent 122 produced by the organisms 130 may still pass through the pores 123. The pores 123 are preferably sized to be as small as possible while still allowing the diffusion of the agent across the membrane 120. Enough nutrient media 132 is supplied to the reservoir 118 to sustain the organisms 130 for an extended period of time. The internal volume of the reservoir 118 and nature of the nutrient media 132 selected should optimize the longevity, reproductive capabilities, health, and number of organisms 130. The reservoir 118 is designed to be safe from rupture. In one embodiment, the organisms 130 may be contained within microspheres to more effectively protect the organisms. The microspheres may be placed directly into the patient's body, without the use of the reservoir 118. In one embodiment, the microspheres may be injected intravenously into the patient's body.

The organisms 130 may be preferably sustained within the reservoir 118 for a period of no less than six months. A lifetime of up to thirty years may be reached. The sustainable duration of the organisms 130 may be varied, based on the scope of treatment desired by the patient, or the severity of the patient's obesity problem. The reservoir 118 may otherwise be configured in any manner discussed in reference to FIG. 8, including an embodiment in which a net charge is produced on a side of the membrane 120 to enhance or impede flow of the active agent, or an embodiment in which the size of the pores 123 is variable due to an applied voltage or environmental factors. The organisms 130, the active agent 122, and the nutrient media 132 may be replenished by any method discussed throughout this application, including replenishment through an access port.

The organisms 130 utilized in the reservoir 118 may comprise bacteria, due to the relatively non-complex structure of bacterial DNA. The bacteria may be engineered to produce a desired active agent 122 as a result of biological engineering of the bacteria's DNA. Prior to the bacteria being implanted in the reservoir 118, a plasmid vector may be introduced into the bacteria containing a strand of DNA that will cause the bacteria to produce the desired active agent 122. The plasmid vector may be formed by splicing a desired sequence of DNA into the plasmid vector. The DNA sequence may be capable of producing the agent of interest, for example, the CCK-8 (cholecystokinin octapeptide) sequence may be used if desired. The DNA sequence is spliced into a vector having the appropriate promoter section. The vector may comprise a bacteriophage vector, a raboviral vector, a lentiviral vector, a plasmid vector, a herpes simplex viral vector, a semliki forest viral vector, a vesicular stomatitis viral vector, a baculoviral vector, an *autographa californica* nuclear polyhedrosis viral vector, and a ribonucleic acid interference (RNAi) via small interfering ribonucleic acids (siRNA). Other vectors may be utilized as desired, to produce an equivalent result. Once the vector has been introduced to the bacteria, the bacteria act as a self-replicating carrier of a vector which codes for the desired active agent. After the vector has been incorporated into the bacterial DNA, the bacteria containing the modified, or chimeric, strand of DNA will be replicated, amplified and reproduced. Methods of producing recombinant DNA are discussed in "AN INTRODUCTION TO GENETIC ANALY- SIS" by Anthony Griffiths, Jeffery Miller, David Suzuki, Richard Lewontin, and William Gelbert. Further information by also be found in "MOLECULAR CELL BIOLOGY" by Harvey Lodish, Arnold Berk, Paul Matsudaira, Chris Kaiser, Monty Krieger, Matthew Scott, S. Lawrence Zipursky, and James Darnell. In one embodiment, electrical energy may be applied to the bacteria to weaken the cell wall of the bacteria. A plasmid is then introduced into the bacterial cell, having a DNA sequence that codes for a desired active agent. The bacterium will express the genes in the plasmid and produce the desired active agent.

Once a stable colony of chimeric bacteria are produced, the bacteria will then be introduced into the reservoir 118, either prior to implantation of the reservoir 118 within the patient's body, or after the reservoir 118 has been implanted. The bacteria may be introduced into the reservoir 118 through a fill valve, for example, one of the fill valves discussed in various embodiments disclosed throughout this application. The active agent produced by the bacteria is selected such that no significant adverse symptoms are produced for the patient. The active agent is introduced to the patient at a rate sufficient to produce the desired treatment effect. In an embodiment wherein cholecystokinin octapeptide is utilized as the active agent, the desired rate of diffusion into the patient's body may be 1.6 picomole per liter per minute. Such a diffusion rate may produce a desired concentration of cholecystokinin octapeptide within the patient's body of 4+/−0.5 picomoles per liter when the patient is fasted, and 8+/−1.5 picomoles per liter when the patient is fed. In an embodiment wherein peptide-tyrosine-tyrosine (3-36) (PYY 3-36) is utilized as the active agent, the desired rate of diffusion into the patient's body may be 0.3182 picomole per liter per minute. Such a diffusion rate may produce a desired concentration of peptide-tyrosine-tyrosine (3-36) within the patient's body of 11+/−1 picomoles per liter when the patient is fasted, and 20+/−1 picomoles per liter when the patient is fed. Such diffusion rates and body concentrations are approximate, and may be varied as desired.

A benefit of utilizing biological organisms 130 to produce the active agent 122 is that the active agent may be replenished within the patient's body over an extended duration of time. A quantity of new active agent 122 is produced by the organisms 130 during the treatment period of the patient, rather than a single quantity of active agent 122 being inserted into the reservoir 118 by a physician and then remaining in the patient's body, and being exposed to the internal body heat of the patient, for an extended duration of time. The biological organisms 130 may extend the effective life of the active agent 122 dispensed into the patient's body. In addition, the organisms 130 may reduce the number of times the reservoir 118 must be refilled.

The embodiments shown in FIGS. 6-9 that utilize a semi-permeable membrane may be incorporated with any of the embodiments shown throughout this application. The semi-permeable membrane may allow for a slow, for example, constant, diffusion of the agent into the body from other locations in the body.

Figure 10:
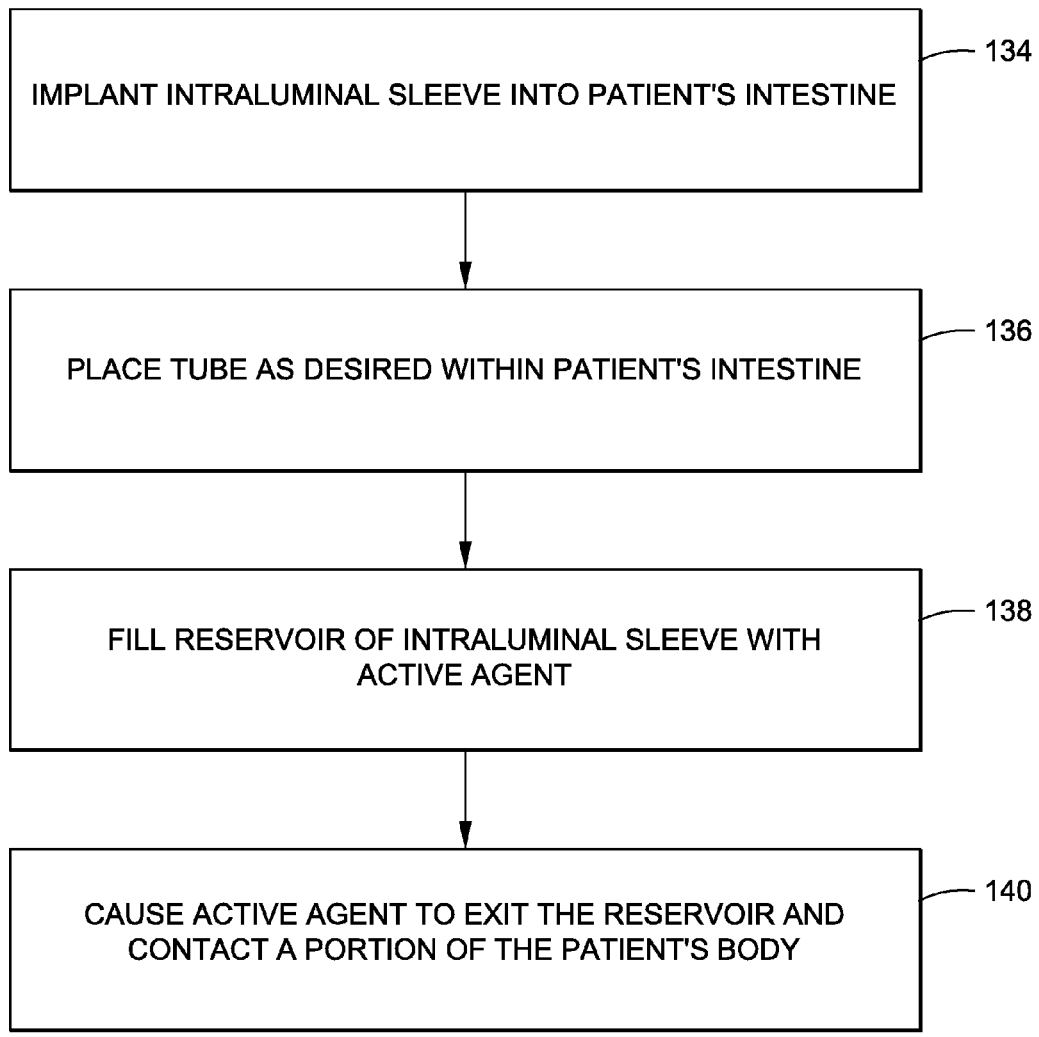
FIG. 10 is a flowchart representing an exemplary method for the treatment of obesity according to one embodiment of the present invention.
Figure 14:
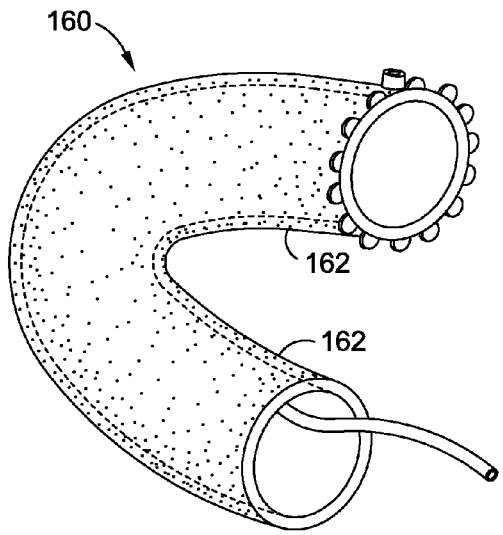
FIG. 14 is a perspective view of an intraluminal sleeve according to one embodiment of the present invention.
Figure 15A:
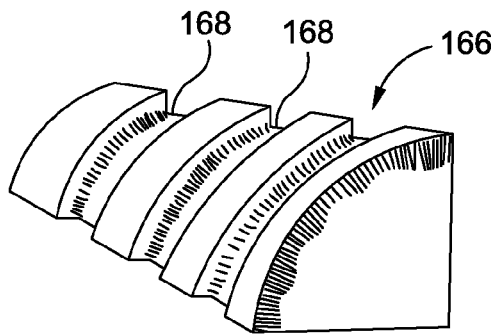
FIGS. 15A and 15B are perspective views of surface structures useful for containing active agents in conjunction with an intraluminal sleeve in accordance with systems of the present invention.
Figure 15B:
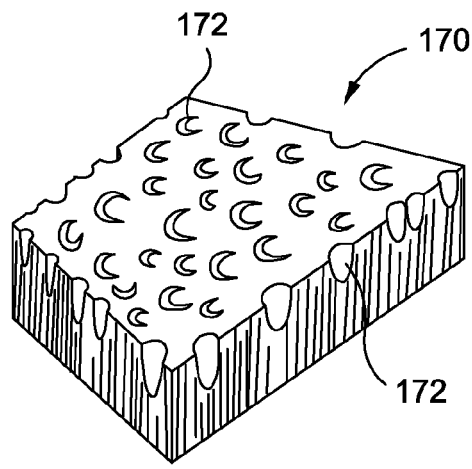
Figure 16:
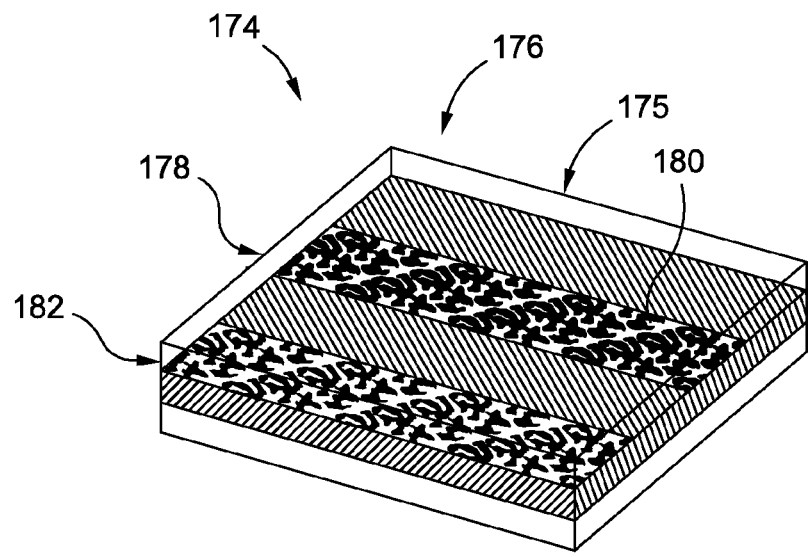
FIG. 16 is a simplified representation of a diffusion material useful for controlling release of active agents in conjunction with an intraluminal sleeve in accordance with systems of the present invention.

FIG. 10 illustrates an exemplary method for the treatment of obesity utilizing any of the intraluminal sleeve system embodiments shown in FIGS. 1-9, and further, any embodiment discussed, infra, in relation to FIGS. 14-16. In step 134, an intraluminal sleeve is implanted within the patient's intestine. The intraluminal sleeve may be placed endoluminally, or through endoluminal means. Endoluminal tools may be utilized to place the intraluminal sleeve into the patient's intestines. The intraluminal sleeve may be inserted into the patient's intestine in a deflated state.

In step 136, a tube, for example a tube 30, 100, shown in FIG. 1-3 or 6-7, may be placed as desired within the patient's intestine. The tube may be placed within the patient's intestine using endoluminal tools.

In step 138, a reservoir, for example a reservoir 28, 66, 90, 114, shown in FIG. 1-3, 4-5, 6 or 7, may be filled with an active agent. The reservoir may be filled through a fill valve coupled to the intraluminal sleeve, or through other appropriate means. A filling mechanism may be utilized to fill the reservoir with fluid, including a fluid containing an active agent. For the embodiment shown in FIG. 9, the filling step may further comprise placing organisms and/or nutrient media into the reservoir. In one embodiment, the reservoir may be filled with the active agent prior to implantation.

In step 140, the physician or patient may cause the active agent to be dispensed from the reservoir, through any of the means discussed throughout this application. For example, the physician may activate a pump to dispense the active agent from the reservoir. In addition, the physician may implant and activate a biological sensor, capable of acting in a feedback loop with the reservoir, as discussed in relation to FIGS. 1-7. The active agent is dispensed to contact the desired portion of the patient's body.

Figure 11:
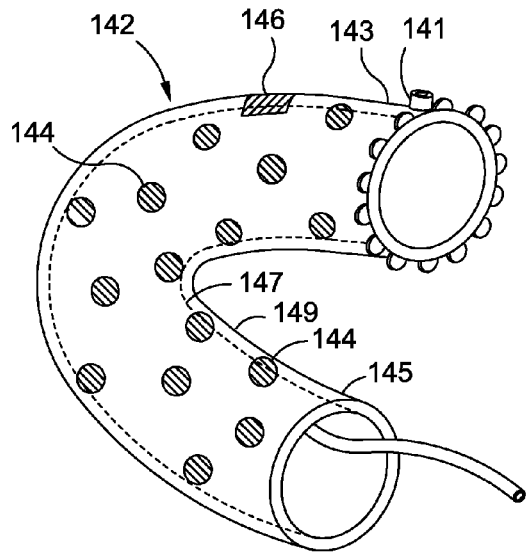
FIG. 11 is a perspective view of an intraluminal sleeve according to one embodiment of the present invention.

FIG. 11 illustrates an embodiment of an intraluminal sleeve 142 having a plurality of electrodes 144 configured to apply electrical energy, or stimulation, to the patient's intestines. The intraluminal sleeve 142 may include a first end 143, and a second end 145, and a reservoir 147, which may be configured similarly as the reservoir shown in FIGS. 2 and 3. A fill valve 141 may be fluidly coupled to the reservoir 147.

The electrodes 144 are positioned on the outer surface 149 of the intraluminal sleeve 142, and are capable of contacting the interior of the patient's intestine, to apply electrical stimulation directly to the patient's intestine. The intraluminal sleeve 142 may further include an electrical control device 146 capable of containing instructions in a memory, which are executed by a processor. The electrical control device 146 may also include a transmitter and receiver, the receiver being capable of receiving instructions from an external transmitter sent wirelessly, to allow the electrical control device 146 to be programmed after implantation. The electrical control device 146 may also be programmable prior to implantation. The instructions stored in the memory may also cause the electrodes 144 to apply electrical stimulation based on a timer or a schedule stored in the memory.

The electrical control device 146 may additionally include a pressure sensor, capable of sensing intestinal activity of the patient. The electrical control device 146 may be positioned to sense a force exerted against the pressure sensor. For example, the sensor may detect forces exerted against the sensor by chyme passing through the intraluminal sleeve 142. The electrical control device 146 may then instruct the electrodes 144 to apply electrical energy to the patient's stomach, in response to the force detected by the control device 146. The electrical control device 146 may be powered, either inductively from a remote device or through a battery (not shown) that may be charged prior to implantation of the intraluminal sleeve 142 or charged inductively after implantation, through appropriate means.

The application of electrical energy to the patient's intestines, used in conjunction with an intraluminal sleeve, may serve to promote satiety signals delivered to the patient's brain. The electrical energy may stimulate local nerves that are normally only stimulated when food passes through the patient's intestines. The electrical impulses may strengthen the intensity of these signals to indicate to the patient's brain that more extensive food consumption has occurred than has actually occurred. The patient may then feel full more quickly, and will reduce food consumption sooner. The use of a pressure sensor in the electrical control device 146 may assure that the enhanced satiety signals are produced when most relevant for the patient, namely, during times of food consumption.

Figure 12:
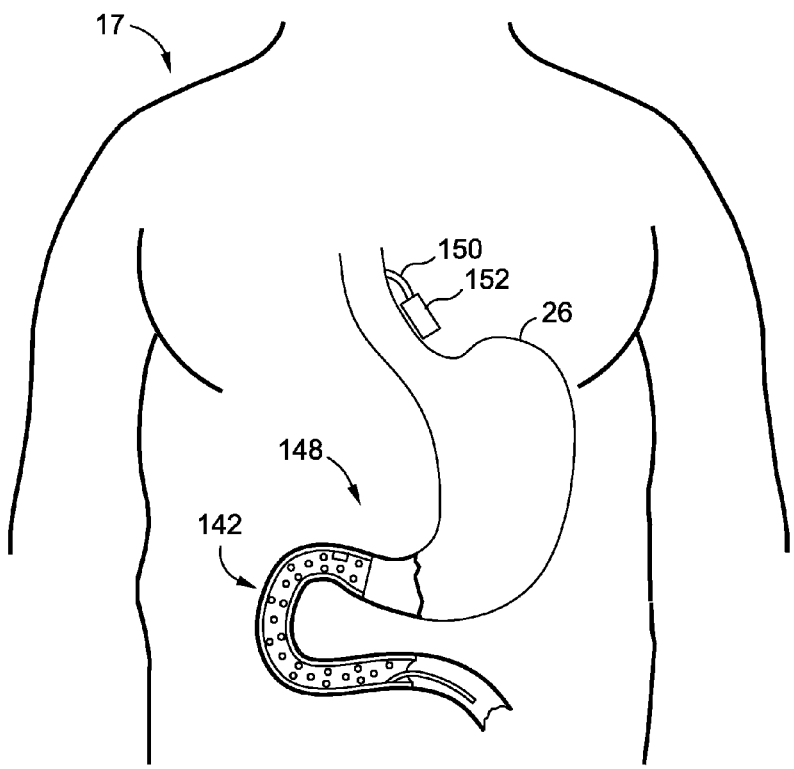
FIG. 12 is a perspective view of a system for the treatment of obesity according to one embodiment of the present invention.

FIG. 12 illustrates an embodiment of an intraluminal sleeve system 148 that includes the intraluminal sleeve 142 shown in FIG. 11, and a plurality of electrodes 150 that couple to the lower third of the patient's esophagus. The electrodes 150 are fixed to the patient's esophagus by known means, including an adhesive, barbs, sutures, or similar other means. The electrodes 150 extend from an electrical control device 152 that is separate from the electrical control device 146 discussed in relation to FIG. 11. The electrodes 150 may comprise thin, wire-like projections extending from the electrical control device 152 in a direction away from the patient's stomach 26. The electrical control device 152 may be configured similarly as the electrical control device 146 positioned on the intraluminal sleeve 142. The electrical control device 152 may be capable of powering the electrodes 150 and causing the electrodes 150 to apply electrical stimulation to the lower third of the patient's esophagus.

The electrical control device 152 may be controlled wirelessly from the control device 146 on the intraluminal sleeve 142. For example, the electrical control device 152 may be configured to receive a signal from the intraluminal sleeve 142, causing the electrodes 150 to apply electrical energy to the lower third of the patient's esophagus. The electrodes 150 may be configured to apply electrical energy to the lower third of the patient's esophagus in response to a force detected by the electrical control device 146. The force may have been exerted against the intraluminal sleeve 142 by chyme passing through the intraluminal sleeve 142. In one embodiment, the electrical control device 152 may be controlled wirelessly from an external controller, for example, the external control device 56 shown in FIG. 17.

A benefit of placing an electrode 150 along the lower third of the esophagus, or lower thoracic esophagus, is to enhance the effect of the electrical stimulation applied to the patient's body. Recent studies suggest direct stimulation to the lower third of the esophagus may produce enhanced stimulation of local nerves, including the vagus nerve, which will enhance the production of satiety signals. The stimulation of the lower third of the esophagus, as opposed to direct simulation of the vagus nerve along other portions of the patient's body, for example, the patient's stomach, offers an improvement over prior known electric stimulation methods. In addition, the use of electrodes along the lower third of the esophagus, in combination with an intraluminal sleeve positioned in the patient's intestine, produces a superior combination of obesity treatments over electrical stimulation alone, or an intraluminal sleeve alone, or electric stimulation of other portions of the vagus nerve, including along the stomach. In one embodiment, the electrode 150 may be placed along the vagus nerve in a position not along the lower third of the esophagus. However, it is understood the position of the electrode 150 along these other portions of the vagus nerve may not include the therapeutic effects of electrodes 150 placed along the lower third of the esophagus.

In one exemplary method of operation, an electrode 150 is inserted laparoscopically within the patient's body. The electrode 150 is then coupled to the lower third of the patient's esophagus, to offer superior production of satiety signals in response to electrical stimulation. The electrode 150 may be powered by an electrical control device 152. The electrical control device 152 may be wirelessly controlled by an electrical control device 146 integrated with the intraluminal sleeve.

Any of the embodiments shown in FIGS. 11-12 may be incorporated with any other embodiment shown throughout this application. For example, electric stimulation in combination with the use of a reservoir of active agent may serve to greatly enhance the production of satiety signals produced in an individual's body. Any combination of treatments may be used as desired to enhance the treatment of obesity.

Figure 13:
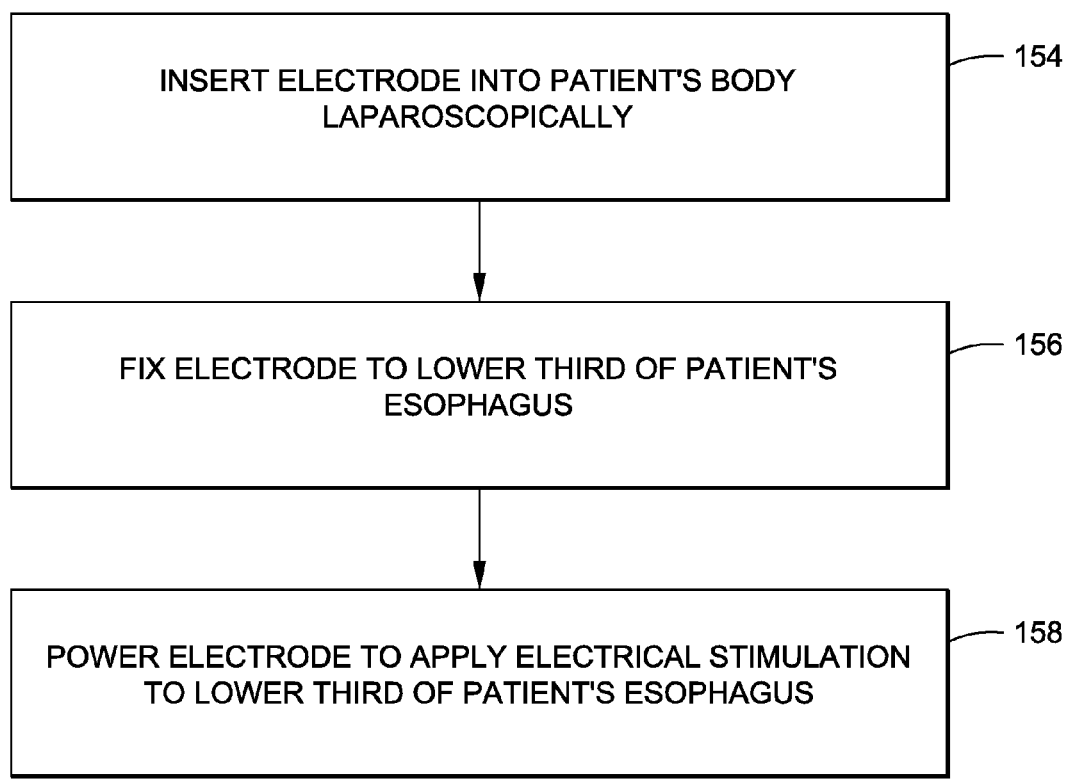
FIG. 13 is a flowchart representing an exemplary method for the treatment of obesity according to one embodiment of the present invention.

FIG. 13 illustrates an exemplary method for the treatment of obesity utilizing the electrical stimulation device embodiment shown in FIG. 12. In step 154, an electrode is inserted within a patient's body laparoscopically, or through laparoscopic means. Laparoscopic tools are utilized to insert the electrode into the patient's body. The electrode may be utilized in combination with an intraluminal sleeve, for example, as shown in FIG. 12. A combination of intraluminal sleeve treatment and electric treatment to the lower third of the patient's esophagus offers superior therapeutic properties than an intraluminal sleeve used alone, or in combination with electric treatment to other portions of the patient's body.

In step 156, the electrode is fixed to the lower third of the patient's esophagus. The electrode may be fixed to the patient's esophagus using barbs, tacks, sutures, adhesives, or the like. If the electrode is coupled to an electrical control device, for example the electrical control device 152 shown in FIG. 12, then the electrical control device may be implanted prior to, at, or after, this step. The electrode may comprise a wire-like projection extending from the electrical control device and connecting to the esophagus. The electrode may be positioned along the portion of the patient's vagus nerve extending along the lower third of the esophagus. In an embodiment including a plurality of electrodes, each electrode may be positioned in sequence along the vagus nerve, or other portions of the lower third of the esophagus. In an embodiment including an intraluminal sleeve, for example, the intraluminal sleeve 142 shown in FIGS. 11 and 12, the intraluminal sleeve may be inserted into the patient's body prior to, at, or after, this step. The intraluminal sleeve may include an electrical control device, for example the electrical control device 146, shown in FIG. 11, which is capable of wireless communication with the electrical control device coupled to the electrode.

In step 158, the electrode is powered to apply electrical stimulation to the lower third of the patient's esophagus. Such power may be delivered via a battery charge, or an inductive charge. The electrical control device, for example, the electrical control device 152, may be powered at this step to allow the electrical control device to cause the electrode to deliver electric stimulation to the lower third of the esophagus.

FIG. 14 illustrates an embodiment of the present invention including an intraluminal sleeve 160 having an ancillary device 162 incorporated into the outer surface 164 of the intraluminal sleeve 160. The ancillary device 162 may include a coating of an active agent placed on the outer surface 164 of the intraluminal sleeve 160. In one embodiment, the ancillary device 162 may form a coating on any surface of the intraluminal sleeve, including an inner surface.

In some embodiments, the ancillary device 162 comprises a composition incorporated into the intraluminal sleeve 160. The composition may comprise a matrix material and an active agent combined with the matrix material, providing a coating of active agent over the surface of the intraluminal sleeve 160. The matrix material may be a biodegradable material, referred to equivalently as a bioerodible material, for example a bioerodible polymer which, during erosion thereof in the body, releases the active agent from the composition, for example, in a controlled manner, for example in a time-release fashion.

Alternatively, the ancillary device 162 may comprise a non-bioerodible material structured to facilitate release of an active agent into the body. In some embodiments, the ancillary device 162 includes structures for containing and releasing active agents, for example, in a controlled manner. In one embodiment, combinations of bioerodible and non-bioerodible materials for containing and releasing active agents are also contemplated.

FIG. 15A illustrates an embodiment of an ancillary device 166 including recessions, pores or grooves capable of containing an agent. Ancillary device 166 may include one or more of the features of the ancillary device 162 described elsewhere herein.

Ancillary device 166 comprises a polymer surface having one or more indentations or grooves 168 capable of containing or holding a satiety inducing agent, or a composition containing a satiety inducing agent, for example, in solid, gel, powder, paste or other form. The ancillary device 166 may form a coating of active agent over the surface of an intraluminal sleeve.

Turning now to FIG. 15B, alternatively or additionally, an ancillary device 170 comprises a polymer surface having a porous or other irregular structure, wherein pores 172 are capable of containing or holding an active agent, or a composition such as a matrix material containing an active agent. The ancillary device 170 may form a coating of active agent over the surface of an intraluminal sleeve.

The ancillary devices 162, 166, 170 may be made of any suitable, biocompatible material, for example, any suitable material approved by the Food and Drug Administration (FDA) for use in humans, for example, as approved for long term administration of agents and long term placement in the body. In one embodiment, the material is ethylene vinyl acetate (EVA).

Referring now to FIG. 16, in some embodiments of the invention, the ancillary device 174 comprises a film or membrane 176 which makes up a surface coating on an intraluminal sleeve, for example, a surface of an intraluminal sleeve which contacts the patient's intestines when the intraluminal sleeve is appropriately positioned. The film 176 is capable of releasing a satiety inducing agent from the intraluminal sleeve and into the patient, for example, at a controlled rate.

For example, the film 176 may comprise a first membrane layer 175 and a second membrane layer 178. The film 176 may further comprise a composition containing a satiety inducing agent, wherein the composition is located adjacent, for example, between the first and second membrane layers 175, 178. The first and second membrane layers 175, 178 may comprise EVA or other suitable polymer or copolymer.

In the embodiment shown in FIG. 16, the film 176 further comprises first and second agent layers 180, 182 which are made up of a composition containing a satiety inducing agent. The first and second agent layers 180, 182 are disposed in an alternating fashion with respect to the first and second membrane layers 175, 178. The membrane layers 176, 178 may have a known diffusion rate relative to the selected satiety inducing agent.

The film 176 is effective to control dosage and delivery of the agents to the patient. The film 176 may therefore have a desired porosity and/or be made of a suitable material so as to provide a controlled release of the agent.

For example, each of the ancillary devices described herein, for example, devices 162, 166, 170 and 174, may be structured to provide effective concentrations of the agent for about six months, or for about one year, about two years, or about three years or more. In some embodiments, the devices 162, 166, 170 and 174 are structured to provide a sustained release rate, for example, of three years followed by a gradually decreasing release rate over the next about two to about three years. The duration of the effective concentration of the agent, and the release rate, may be varied as desired. Numerous release protocols are contemplated by the inventors, and are understood to fall within the scope of the present invention.

In one embodiment, the agent could also be applied to the intraluminal sleeve via a slow release drug eluting coating similar to coatings used on cardiovascular stents such as the Cordis Sirolimus Drug eluting stent or the contraceptive device Norplant. The coating could be applied directly to the intraluminal sleeve for a slow release of the drug into the body.

FIG. 17 illustrates an embodiment of an intraluminal sleeve system 184 used for the treatment of obesity. The system 184 includes the sensor 14 and an external control device 56, which may be operated by the patient or by a physician, each equivalently referred to as the user in this application. The system 184 preferably includes an intraluminal sleeve 186, which may be configured similarly as the intraluminal sleeve 12 shown in FIGS. 1-3. For example, the intraluminal sleeve 186 may include a reservoir configured to dispense an active agent. The use of an intraluminal sleeve 186 in combination with the therapeutic actions discussed in relation to the system 184 (e.g., application of a patch, drinking of a liquid) is designed to treat obesity in the patient to a greater degree than a treatment solely involving an intraluminal sleeve.

The external control device 56 may comprise a handheld device that may be carried by the patient, or may be used by the physician. The external control device 56 may also comprise any other electrical device used external to the patient, and capable of receiving and/or transmitting information to the sensor 14. The external control device 56 may include a transmitter, a receiver, a processor and a memory. The external control device 56 may additionally include an alerting system, which may comprise an auditory alarm or notification, or a visual stimulation or notification, such as a light or a reading on a display screen, or a physical alerting system, including movement of the external control device 56, such as a vibration. The memory may store instructions, executed by the processor. The instructions may cause the control device 56 to perform any of the operations discussed throughout this application. The external control device 56 may also include input means, such as a keypad, for the user to input instructions into the control device 56.

The receiver of the control device 56 may include an antenna capable of receiving signals sent from the sensor 14. The signal may provide information to a user, informing the user about the readings of the sensor 14. For example, the control device 56 may alert the user to take action in response to the signal sent from the sensor 14. The signal transmitted from the sensor 14 may indicate to the external control device 56 that a biological characteristic, such as a hormone level, is below a threshold value for the patient. The external control device 56 may then provide a notification, or publish certain responses to the user, for the user to take action, in response to the biological characteristic sensed by the sensor. The action preferably is effective to vary the biological characteristic sensed by the sensor. The notification, or publication, may utilize the alerting system, which may involve the sounding of an alarm, or a message presented on a display for the user to take action.

In response to the alert from the control device 56, the user may take a series of actions. Generally, the actions are designed to respond to the alert provided by the control device 56. For example, if the alert indicates a low hormone level in the patient, then the user may perform such actions that will increase the hormone level.

One such action may include injecting the patient with an active agent, possibly with a syringe. The injection may be a manual injection directly into the body of the patient. The control device 56 may alert the patient to inject the patient's body with a syringe during routine times. The injections may be performed under physician or patient control. The injections could occur routinely, or as advised by the control device 56.

Another action may include increasing the hormone level of the patient through a patch placed on the skin of the patient. The patch may have an active agent on one side of the patch, and may be capable of slowly diffusing the active agent through the patient's skin. The patch could be replaced routinely, or as advised by the control device 56.

Another action may include the patient inhaling an active agent, either through the nose or mouth or spraying an active agent into the nose or mouth. A nasal spray may allow the vaporous active agent to be applied to the nasal canal for immediate absorption. The active agent would be received by the patient closer to the satiety centers of the brain. An inhalant would allow the vaporous active agent to be absorbed into the lungs. The inhalant or spray could be administered routinely, or as advised by the control device 56.

Another action may include the patient drinking a liquid including an active agent. The active agent may be absorbed in the mouth, esophagus, or further down the gastrointestinal tract. A liquid may also be sprayed into the patient's mouth. The liquid could be administered routinely, or as advised by the control device 56.

Another action may include the patient swallowing a pill containing a desired active agent. In one embodiment, the pill may be coated to allow for slow, continuous or timed release. In one embodiment, the pill may be coated to react when in combination with a certain pH to allow it to pass into a specific location of the gastrointestinal tract. In one embodiment, the pill may have multiple mini-spheres of active agent coated with a variety of coatings controlled by pH to allow for the active agent to be released throughout the gastrointestinal tract. The pill could be administered routinely, or as advised by the control device 56.

Another action may include the user placing an orally received substance within the patient's mouth, including a film or gum that may introduce an active agent into the patient's body. The substance may be placed under the patient's tongue, and introduced into the patient's body through the local mucous membranes beneath the tongue. A chewing gum may allow the active agent to be absorbed by the mucous membranes within the patient's mouth. The orally received substance could be administered routinely, or as advised by the control device 56.

The actions, performed in combination with an intraluminal sleeve therapy, will provide for a superior treatment of obesity during the duration of the treatment, in contrast to use an intraluminal sleeve alone, or the actions performed alone.

The external control device 56 may be configured to select an appropriate alert in response to the signal sent from the sensor 14. For example, the control device 56 may be programmed to determine if the sensor 14 has indicated a hormone level is too high, and will alert the user to reduce hormone intake. In addition, the control device 56 may be programmed to determine if the sensor 14 has indicated a hormone level is too low, and will alert the user to increase hormone intake, in any form. The control device 56 may be configured to program the threshold detection level into the sensor 14, as discussed in relation to FIGS. 1-3.

In one embodiment, the control device 56 may be configured to instruct the user on which particular action to take, based on the readings of the sensor 14. For example, the control device 56 may select whether the patient should ingest a pill having a hormone, or chew a gum having a hormone, based on the signal sent from the control device 56. The particular action selected may be based on the degree to which the biological characteristic deviates from a threshold value, or based on a schedule of therapy designed for the patient, by, for example, the physician.

In one embodiment, the sensor 14 may be incorporated with an intraluminal sleeve device, to provide local readings of a desired biological characteristic for the patient. The sensor 14 may telemetrically send signals to the control device 56 using a transmitter integrated with the sensor 14.

The external control device 56 may be used with various other embodiments of systems for the treatment of obesity discussed throughout this application. For example, the transmitter of the external control device may be used to transmit signals to the controller 54, discussed in relation to FIGS. 3, 5, 6 and 7. The external control device 56 may be capable of causing the output device 52 (shown in FIGS. 3, 5, 6 and 7) to emit, or not emit, the active agent into the patient's body, in response to instructions sent from the external control device 56. The external control device 56 may be capable of setting the rate at which the output device 52 dispenses the active agent from the reservoir. The external control device 56 may be capable of programming an active agent dispersion schedule into the controller 54. In addition, the sensor 14, external control device 56, and controller 54, may act in a closed loop, wherein the sensor 14 senses a biological parameter of the patient, and sends a signal to the external control device 56 that indicates to the user to take a specified action. The user may then instruct the controller 54 to distribute the active agent from the reservoir. In addition, the sensor 14 may cause the controller 54 to distribute the active agent from the reservoir without the intervention of the user. The external control device 56, however, may receive notification that the controller 54 is automatically distributing the active agent in response to the sensed biological parameter. The external control device 56 may give the user the opportunity to intervene, and prevent the automatic distribution of the active agent, or enhance the distribution of the active agent.

In one embodiment, the system 184 includes an external distribution device 188 that may be positioned external to the patient's body. The distribution device 188 may comprise a reservoir for holding an active agent that is capable of being injected into the patient's body, or pumped into the patient's body through a tube. The distribution device 188 may be capable of accurately metering the volume and rate at which the active agent is injected into the body. The external distribution device 188 may receive signals directly from the sensor 14 instructing the device 188 to distribute the active agent to the patient's body. The external distribution device 188 may automatically distribute the active agent to the body in response to this signal, or may produce an alert to the user instructing the user to take action. The user may cause the external distribution device 188 to dispense the active agent to the patient's body in response to the signal from the sensor 14. A benefit of the external distribution device 188 is that the active agent may be refilled by the patient, or physician, without having to insert endoluminal tools to fill the intraluminal sleeve. The patient could load and self-administer the external distribution device 188.

In one embodiment, the actions taken in response to the alert from the control device 56 may be performed solely, or without prompting from the control device 56. For example, the patient may undergo an obesity treatment including the placement of an intraluminal sleeve in the patient's stomach, in combination with the use of an active agent, that is introduced into the patient's body through a syringe, or a patch, or an inhalant or spray, or a liquid to be consumed by the patient, or a pill, or a film or a chewing gum introduced into the patient's mouth. The combination of the intraluminal sleeve and the actions that introduce the active agent into the patient's body may produce a superior treatment for obesity, in comparison to treatment with an intraluminal sleeve alone. In one embodiment, a patient may treat obesity by performing the above-listed actions, including the use of an active agent that is introduced into the patient's body through a syringe, or a patch, or an inhalant or spray, or a liquid to be consumed by the patient, or a pill, or a film or a chewing gum introduced into the patient's mouth. The actions may be performed without the use of an intraluminal sleeve.

Any of the embodiments discussed in relation to FIG. 17 may be incorporated with any other embodiment shown throughout this application. For example, a treatment involving insertion of chewing gum into the patient's mouth may be used in combination with electric stimulation, and/or a reservoir of active agent positioned within the patient's body, and/or an ancillary device incorporated in any structure of the system. Any combination of treatments discussed throughout this application may be used as desired to enhance the treatment of obesity.

Example of GLP-1

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing glucagon like peptide 1 (GLP-1) that is released at a rate to achieve plasma concentrations of $[10\text{-}30 \text{ pMol/L}]_p$ GLP-1 over a period of 3-24 months. A reservoir containing glucagon like peptide 1 (GLP-1), according to any of the embodiments of this application may also be utilized. An injection, liquid, pill, spray, inhalant, patch, or oral substance such as a gum containing glucagon like peptide 1 (GLP-1) may also be used. The patient reports a marked suppression of appetite, and within 12 months, the patient has lost 58 pounds.

Example of OXM

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing oxyntomodulin (OXM) that is released at a rate to achieve plasma concentrations of $[105\text{-}150 \text{ pMol/L}]_p$ OXM over a period of 3-24 months. A reservoir containing oxyntomodulin (OXM), according to any of the embodiments of this application may also be utilized. An injection, liquid, pill, spray, inhalant, patch, or oral substance such as a gum containing oxyntomodulin (OXM) may also be used. The patient reports a marked suppression of appetite, and within 12 months, the patient has lost 58 pounds.

Example of PYY

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Peptide Y-Y (PYY) that is released at a rate to achieve plasma concentrations of $[10\text{-}55 \text{ pMol/L}]_p$ PYY over a period of 3-24 months. A reservoir containing Peptide Y-Y (PYY), according to any of the embodiments of this application may also be utilized. An injection, liquid, pill, spray, inhalant, patch, or oral substance such as a gum containing Peptide Y-Y (PYY) may also be used. The patient reports a marked suppression of appetite, and within 12 months, the patient has lost 58 pounds.

Example of PP

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Pancreatic Peptide (PP) that is released at a rate to achieve plasma concentrations of $[150\text{-}300 \text{ pMol/L}]_p$ PP over a period of 3-24 months. A reservoir containing Pancreatic Peptide (PP), according to any of the embodiments of this application may also be utilized. An injection, liquid, pill, spray, inhalant, patch, or oral substance such as a gum containing Pancreatic Peptide (PP) may also be used. The patient reports a marked suppression of appetite, and within 12 months, the patient has lost 58 pounds.

Example of Insulin

A 49 year old male patient, having a body weight of 322 pounds and a height of 5'11", complains to his physician that he has tried unsuccessfully to lose weight over the past 15 years and is concerned about the effect his excess weight may have on his health. His physician suggests a procedure intended to provide the patient's body with better control over its blood sugars. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Insulin that is released at a rate to achieve plasma concentrations of $[5\text{-}30 \text{ }\mu\text{U/mL}]_p$ Insulin over a period of 3-24 months. A reservoir containing Insulin, according to any of the embodiments of this application may also be utilized. An injection, liquid, pill, spray, inhalant, patch, or oral substance such as a gum containing Insulin may also be used. The patient reports euglycemic effects, or better control by his body of blood sugars.

Example of Leptin

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Leptin that is released at a rate to achieve plasma concentrations of *[3-10 ng/mL]$_p$ Leptin over a period of 3-24 months. A reservoir containing Leptin, according to any of the embodiments of this application may also be utilized. An injection, liquid, pill, spray, inhalant, patch, or oral substance such as a gum containing Leptin may also be used. The patient reports a marked suppression of appetite, and within 12 months, the patient has lost 58 pounds.

*In the case of a female patient the goal plasma concentrations would be [10-20 ng/mL]$_p$.

Example of Amylin

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Amylin that is released at a rate to achieve plasma concentrations of [20-25 pMol/L]$_p$ Amylin over a period of 3-24 months. A reservoir containing Amylin, according to any of the embodiments of this application may also be utilized. An injection, liquid, pill, spray, inhalant, patch, or oral substance such as a gum containing Amylin may also be used. The patient reports a marked suppression of appetite, and within 12 months, the patient has lost 58 pounds.

Example of CCK

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Cholecystokinin (CCK) that is released at a rate to achieve plasma concentrations of [5-10 pMol/L]$_p$ CCK over a period of 3-24 months. A reservoir containing Cholecystokinin (CCK), according to any of the embodiments of this application may also be utilized. An injection, liquid, pill, spray, inhalant, patch, or oral substance such as a gum containing Cholecystokinin (CCK) may also be used. The patient reports a marked suppression of appetite, and within 12 months, the patient has lost 58 pounds.

Example of CNTF

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Ciliary neuro-trophic factor (CNTF) that is released at a rate to achieve plasma concentrations of [25-1300 pg/dL]$_p$ CNTF over a period of 3-24 months. A reservoir containing Ciliary neuro-trophic factor (CNTF), according to any of the embodiments of this application may also be utilized. An injection, liquid, pill, spray, inhalant, patch, or oral substance such as a gum containing Ciliary neuro-trophic factor (CNTF) may also be used. The patient reports a marked suppression of appetite, and within 12 months, the patient has lost 58 pounds.

Example of CART

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing Cocaine-Amphetamine Regulated Transcript (CART) that is released at a rate to achieve plasma concentrations of [50-250 pM]$_p$ CART over a period of 3-24 months. A reservoir containing Cocaine-Amphetamine Regulated Transcript (CART), according to any of the embodiments of this application may also be utilized. An injection, liquid, pill, spray, inhalant, patch, or oral substance such as a gum containing Cocaine-Amphetamine Regulated Transcript (CART) may also be used. The patient reports a marked suppression of appetite, and within 12 months, the patient has lost 58 pounds.

Example of Ghrelin Inhibition/Antagonism

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing a drug that is released at a rate to achieve plasma concentrations of Ghrelin at [15-30 pg/mL]$_p$ over a period of 3-24 months. A reservoir containing Ghrelin blocker, according to any of the embodiments of this application may also be utilized. An injection, liquid, pill, spray, inhalant, patch, or oral substance such as a gum containing Ghrelin blocker may also be used. The patient reports a marked suppression of appetite, and within 12 months, the patient has lost 58 pounds.

Example of NPY Inhibition/Antagonism

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing a drug that is released at a rate to achieve plasma concentrations of Neuro-peptide Y (NPY) at $[65\text{-}95 \text{ pMol/L}]_p$ over a period of 3-24 months. A reservoir containing Neuro-peptide Y (NPY) antagonists, according to any of the embodiments of this application may also be utilized. An injection, liquid, pill, spray, inhalant, patch, or oral substance such as a gum containing Neuro-peptide Y (NPY) antagonists may also be used. The patient reports a marked suppression of appetite, and within 12 months, the patient has lost 58 pounds.

Example of Orexin A Inhibition/Antagonism

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing a drug that is released at a rate to achieve plasma concentrations of Orexin A at $[20\text{-}50 \text{ pg/mL}]_p$ over a period of 3-24 months. A reservoir containing Orexin A antagonists, according to any of the embodiments of this application may also be utilized. An injection, liquid, pill, spray, inhalant, patch, or oral substance such as a gum containing Orexin A antagonists may also be used. The patient reports a marked suppression of appetite, and within 12 months, the patient has lost 58 pounds.

Example of AgRP Inhibition/Antagonism

A 49 year old male patient, having a body weight of 322 pounds and a height of 5'11", complains to his physician that he has tried unsuccessfully to lose weight over the past 15 years and is concerned about the effect his excess weight may have on his health. At the physician's directive, the patient undergoes a procedure to implant an intraluminal sleeve in his small intestines, having a porous intestines-contacting surface, or having a slowly drug eluting membrane, or having a dissolvable film, or an intraluminal sleeve with small grooves, containing a drug that is released at a rate to achieve plasma concentrations of AgRP at $[1\text{-}16 \text{ ng/dL}]_p$ over a period of 3-24 months. A reservoir containing AgRP antagonists, according to any of the embodiments of this application may also be utilized. An injection, liquid, pill, spray, inhalant, patch, or oral substance such as a gum containing AgRP antagonists may also be used. The patient reports a marked suppression of appetite, and within 12 months, the patient has lost 58 pounds.

Although the invention has been described and illustrated with a certain degree of particularity, it is to be understood that the present disclosure has been made only by way of example, and that numerous changes in the combination and arrangement of parts can be resorted to by those skilled in the art without departing from the scope of the invention, as hereinafter claimed. For example, any of the obesity treatment methods, systems, and devices discussed throughout this application may be used singularly, or in combination, as desired.

The foregoing disclosure is illustrative of the present invention and is not to be construed as limiting the invention. Although one or more embodiments of the invention have been described, persons skilled in the art will readily appreciate that numerous modifications could be made without departing from the spirit and scope of the present invention. It should be understood that all such modifications are intended to be included within the scope of the invention.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An implantable intraluminal sleeve system for the treatment of obesity comprising:
    an intraluminal sleeve configured to be positioned in a patient's intestine and dispense an active agent to the patient that is effective, when released into the patient, to at least assist in effecting weight loss in the patient, wherein the intraluminal sleeve includes a reservoir configured to contain the active agent, the reservoir having an outlet configured to allow the active agent to exit the reservoir and contact a portion of the patient's body, and the outlet of the reservoir is an outer surface of the reservoir that includes a semi-permeable membrane; and
    an electrode configured to produce an electrical charge on a side of the semi-permeable membrane, to enhance or impede diffusion of the active agent through the semi-permeable membrane.

2. The system of claim 1 wherein the intraluminal sleeve forms a flexible cylinder having a first end and a second end, and having an outer surface, and an inner surface that defines an internal lumen of the intraluminal sleeve.

3. The system of claim 2 wherein the first end includes an anchor device configured to fix the first end to a portion of the patient's duodenum.

4. The system of claim 1 further comprising an active agent.

5. The system of claim 4 wherein the active agent is selected from a group consisting of Glucagon-like peptide (GLP-1), Oxyntomodulin (OXM), Peptide YY (PYY), Pancreatic Polypeptide (PP), Insulin, Leptin, Gastrin, Gherlin blocker, inhibitors of DPP-IV, Amylin, Cholecystokinin (CCK), Pro-opiomelanocortin (POMC), and combinations thereof.

6. The system of claim 1 wherein the intraluminal sleeve has an outer wall, and an inner wall that defines an internal lumen of the intraluminal sleeve, the reservoir being positioned within the outer wall of the intraluminal sleeve.

7. The system of claim 6 wherein an outer wall of the reservoir defines at least a portion of the outer wall of the intraluminal sleeve, and an inner wall of the reservoir defines at least a portion of the inner wall of the intraluminal sleeve.

8. The system of claim 1 wherein the intraluminal sleeve includes a tube having a first end coupled to the outlet and a second end configured to dispense the active agent from the reservoir to the portion of the patient's body.

9. The system of claim 1 wherein the outlet includes a one-way valve.

10. The system of claim 9 wherein the one-way valve is configured to allow the active agent to exit the reservoir in response to a force exerted against the reservoir by chyme passing through the intraluminal sleeve.

11. The system of claim 1 wherein the outlet includes a pump.

12. The system of claim 11 further comprising a sensor configured to detect a hormone level of the patient.

13. The system of claim 12 wherein the sensor is configured to transmit a signal to the pump in response to a hormone level detected by the sensor.

14. The system of claim 1 further comprising an electrode configured to apply a voltage to the semi-permeable membrane.

15. The system of claim 14 wherein the voltage causes a size of a pore of the semi-permeable membrane to vary.

16. The system of claim 1 wherein the semi-permeable membrane is made from a material having a property that causes a size of a pore of the semi-permeable membrane to vary automatically in response to an environmental condition in the patient's body.

17. The system of claim 1 wherein the reservoir stores bacteria that produce the active agent.

18. The system of claim 17 wherein pores of the semi-permeable membrane are sized to prevent the bacteria from exiting the reservoir.

19. The system of claim 1 wherein a surface of the intraluminal sleeve includes a coating of the active agent.

20. The system of claim 1 wherein a surface of the intraluminal sleeve includes grooves configured to contain the active agent.

21. The system of claim 1 wherein a surface of the intraluminal sleeve includes pores configured to contain the active agent.

* * * * *